(12) United States Patent
Minskoff et al.

(10) Patent No.: US 8,518,018 B2
(45) Date of Patent: Aug. 27, 2013

(54) APPARATUS AND METHOD FOR ELECTROSURGICAL SUCTION

(76) Inventors: Noah Mark Minskoff, Salt Lake City, UT (US); Nathan Andrew Terry, San Francisco, CA (US)

( * ) Notice: Subject to any disclaimer, the term of this patent is extended or adjusted under 35 U.S.C. 154(b) by 50 days.

(21) Appl. No.: 13/021,596

(22) Filed: Feb. 4, 2011

(65) Prior Publication Data
US 2012/0203208 A1    Aug. 9, 2012

(51) Int. Cl.
*A61M 1/00*    (2006.01)

(52) U.S. Cl.
USPC .............................. 604/540; 606/27; 606/28

(58) Field of Classification Search
None
See application file for complete search history.

(56) References Cited

U.S. PATENT DOCUMENTS

| | | | |
|---|---|---|---|
| D232,591 S | 8/1974 | Haberman et al. | |
| 3,974,833 A | 8/1976 | Durden | |
| D249,549 S | 9/1978 | Pike | |
| D253,247 S | 10/1979 | Gill | |
| 4,204,328 A * | 5/1980 | Kutner | 433/29 |
| 4,347,842 A | 9/1982 | Beale | |
| D270,372 S | 8/1983 | Russo et al. | |
| 4,553,957 A | 11/1985 | Williams et al. | |
| 4,562,838 A | 1/1986 | Walker | |
| D287,879 S | 1/1987 | Braxton et al. | |
| 4,719,914 A | 1/1988 | Johnson | |
| D301,739 S | 6/1989 | Turner et al. | |
| 4,919,129 A | 4/1990 | Weber et al. | |
| 4,943,290 A | 7/1990 | Rexroth et al. | |
| 5,055,100 A | 10/1991 | Olsen | |
| 5,071,418 A | 12/1991 | Rosenbaum | |
| 5,085,657 A | 2/1992 | Ben-Simhon | |
| 5,133,714 A | 7/1992 | Beane | |
| D330,253 S | 10/1992 | Burek | |
| 5,154,709 A | 10/1992 | Johnson | |
| 5,181,916 A | 1/1993 | Reynolds et al. | |
| 5,192,267 A | 3/1993 | Shapira et al. | |
| 5,224,944 A | 7/1993 | Elliott | |
| 5,234,428 A | 8/1993 | Kaufman | |
| 5,242,442 A | 9/1993 | Hirschfeld | |
| 5,244,462 A | 9/1993 | Delahuerga et al. | |
| 5,246,440 A | 9/1993 | Van Noord | |
| 5,269,781 A | 12/1993 | Hewell | |
| 5,295,956 A * | 3/1994 | Bales et al. | 604/30 |
| 5,318,565 A | 6/1994 | Kuriloff et al. | |
| D351,227 S | 10/1994 | Patton et al. | |
| 5,360,427 A | 11/1994 | Majlessi | |
| 5,395,312 A | 3/1995 | Desai | |
| 5,413,575 A | 5/1995 | Haenggi | |
| 5,431,650 A | 7/1995 | Cosmescu | |
| 5,451,223 A | 9/1995 | Ben-Simhon | |
| 5,460,602 A | 10/1995 | Shapira | |
| D370,731 S | 6/1996 | Corace et al. | |
| D373,190 S | 8/1996 | Monson | |

(Continued)

OTHER PUBLICATIONS

International Search Report and Written Opinion of PCT/US2012/023673 issued Jun. 28, 2012, 8 pages.

*Primary Examiner* — Jackie Ho
*Assistant Examiner* — Eric Bryant
(74) *Attorney, Agent, or Firm* — The Neudeck Law Firm, LLC

(57) ABSTRACT

A suction apparatus evacuates the surgical smoke. For example, the suction apparatus may be arranged adjacent to an electrocautery electrode, which may generate smoke during operation, for evacuating smoke from a surgical site. The suction apparatus may include replaceable suction tips that correspond in shape to differently shaped electrocautery electrodes.

20 Claims, 30 Drawing Sheets

(56) References Cited

U.S. PATENT DOCUMENTS

| | | |
|---|---|---|
| D384,148 S | 9/1997 | Monson |
| 5,674,219 A | 10/1997 | Monson et al. |
| 5,693,044 A | 12/1997 | Cosmescu |
| D393,067 S | 3/1998 | Geary et al. |
| 5,800,431 A | 9/1998 | Brown |
| D399,314 S | 10/1998 | Wells et al. |
| 5,830,214 A | 11/1998 | Flom et al. |
| 5,836,909 A | 11/1998 | Cosmescu |
| 5,836,944 A | 11/1998 | Cosmescu |
| D402,030 S | 12/1998 | Roberts et al. |
| 5,951,548 A | 9/1999 | DeSisto et al. |
| D426,883 S | 6/2000 | Berman et al. |
| 6,099,525 A | 8/2000 | Cosmescu |
| 6,117,134 A | 9/2000 | Cunningham et al. |
| 6,142,995 A | 11/2000 | Cosmescu |
| D453,222 S | 1/2002 | Garito et al. |
| 6,355,034 B2 | 3/2002 | Cosmescu |
| 6,616,658 B2 | 9/2003 | Ineson |
| 6,702,812 B2 | 3/2004 | Cosmescu |
| 7,118,570 B2 * | 10/2006 | Tetzlaff et al. .................. 606/48 |
| 7,172,592 B2 | 2/2007 | DeSisto |
| D547,864 S | 7/2007 | Rau et al. |
| D547,867 S | 7/2007 | Malis et al. |
| 7,241,294 B2 | 7/2007 | Reschke |
| 7,303,559 B2 | 12/2007 | Peng et al. |
| 7,537,594 B2 | 5/2009 | Sartor |
| 2005/0113825 A1 | 5/2005 | Cosmescu |
| 2006/0264928 A1 | 11/2006 | Kornerup et al. |
| 2007/0129722 A1 | 6/2007 | Cosmescu |
| 2009/0062791 A1 | 3/2009 | Lee et al. |

* cited by examiner

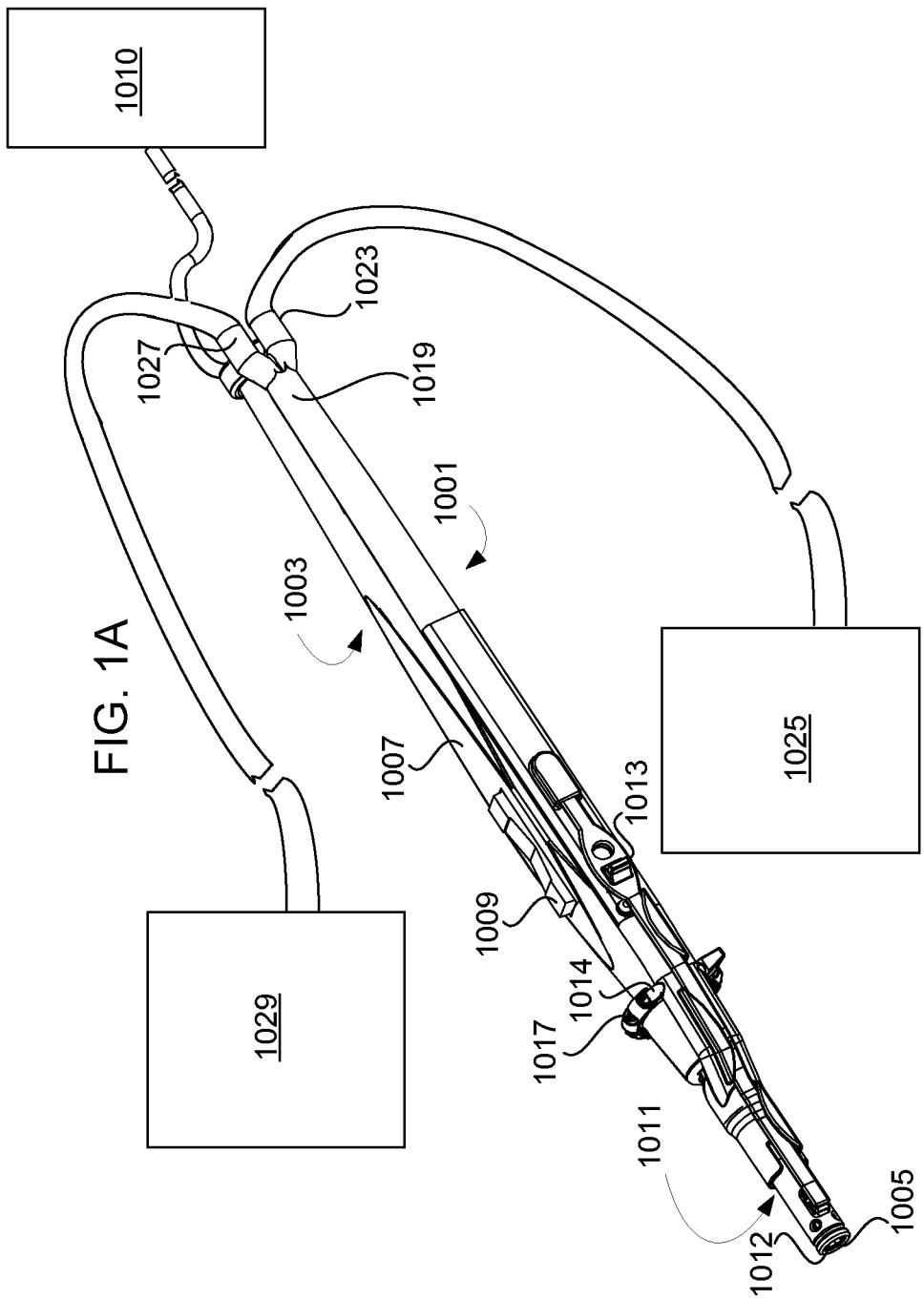

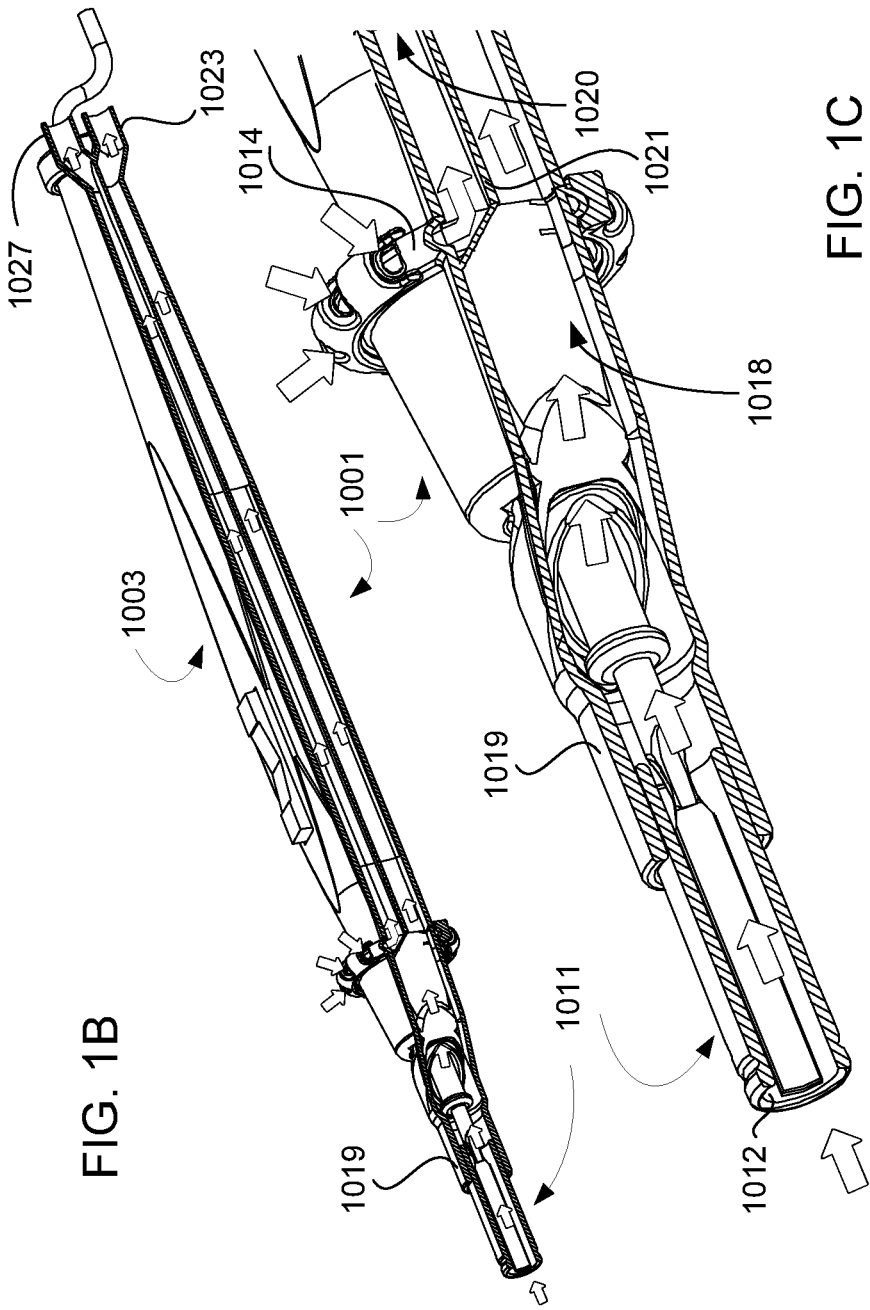

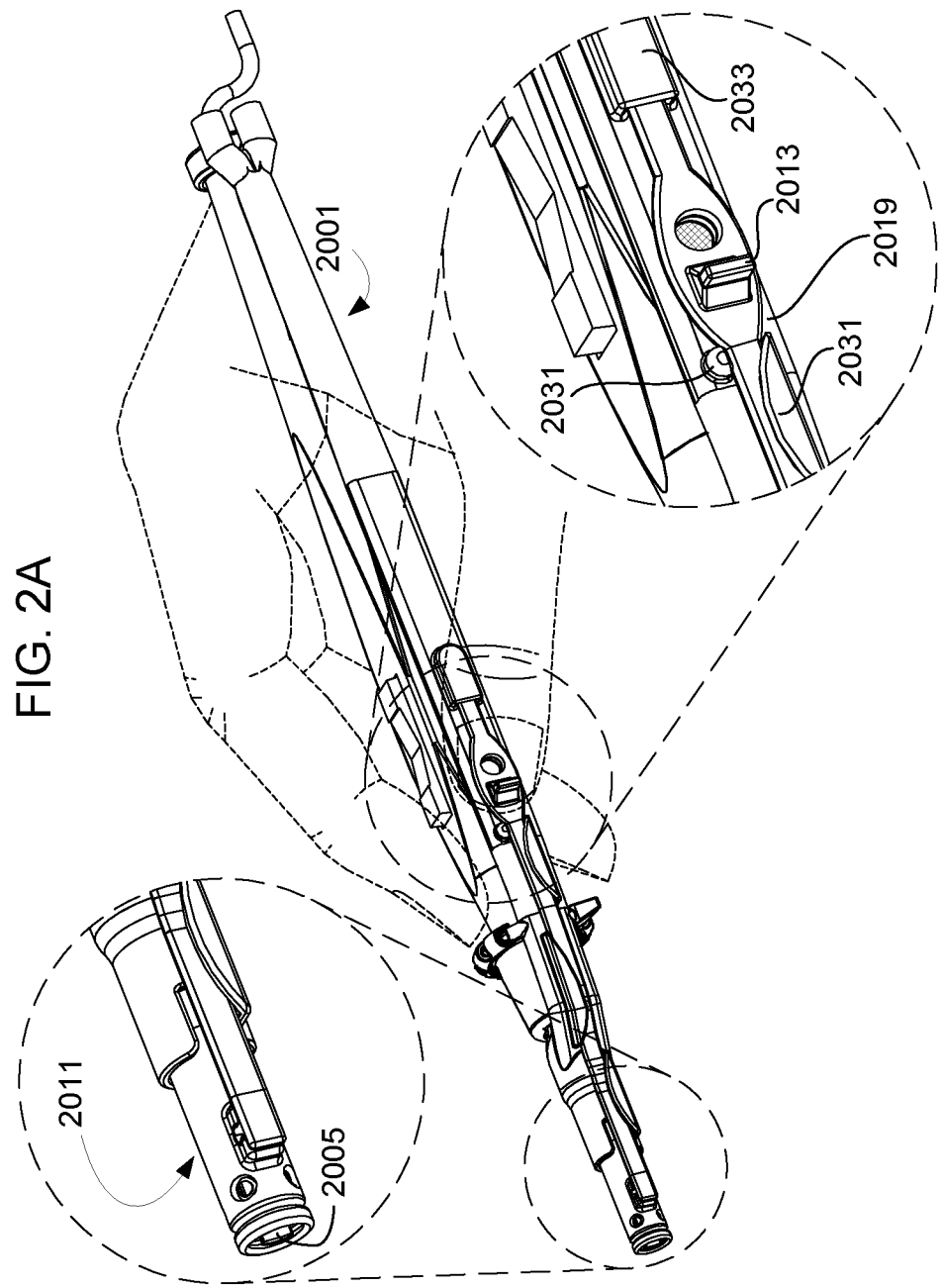

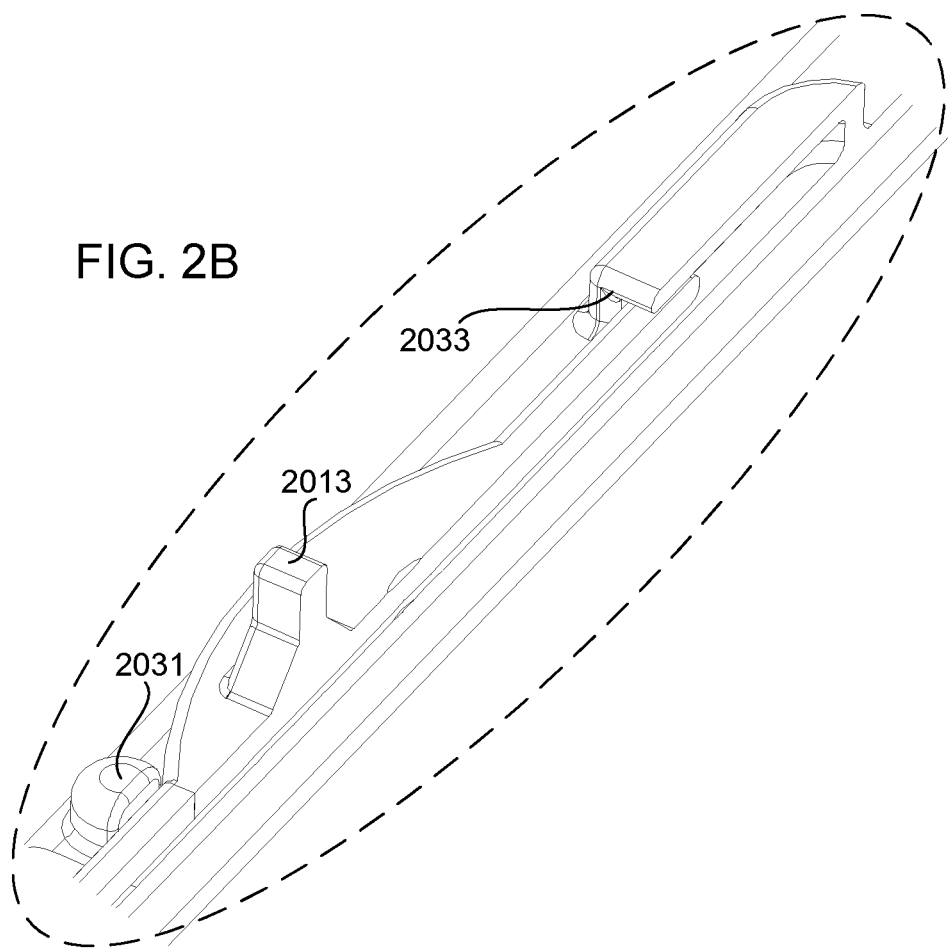

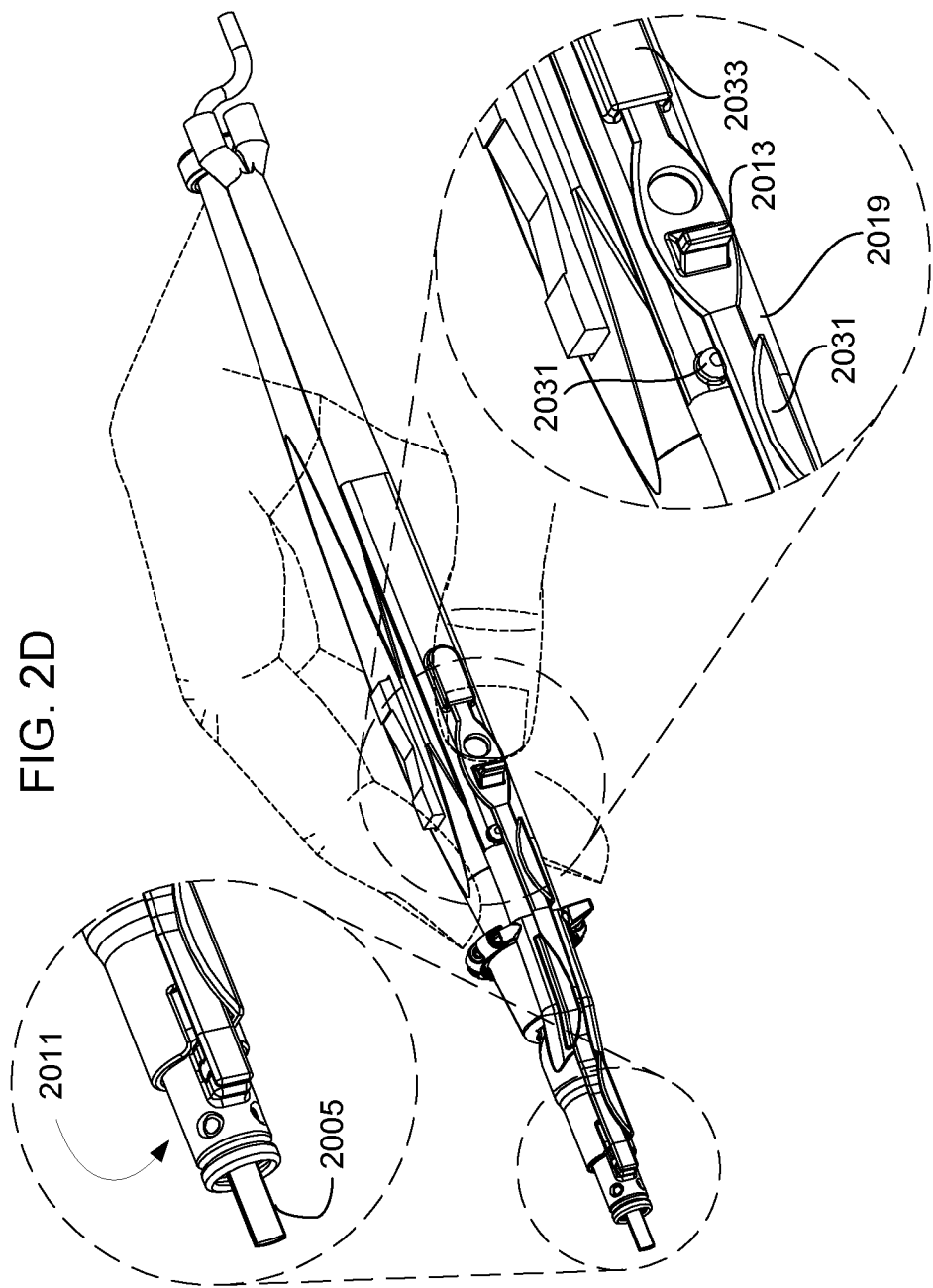

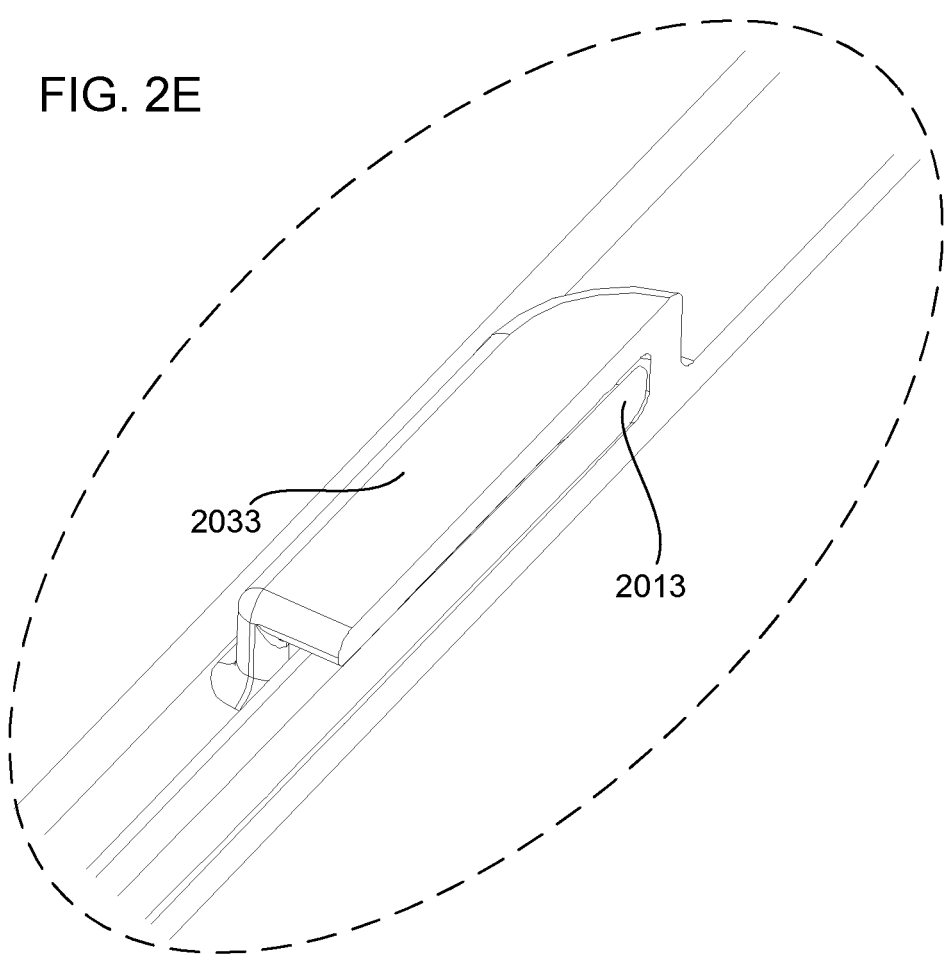

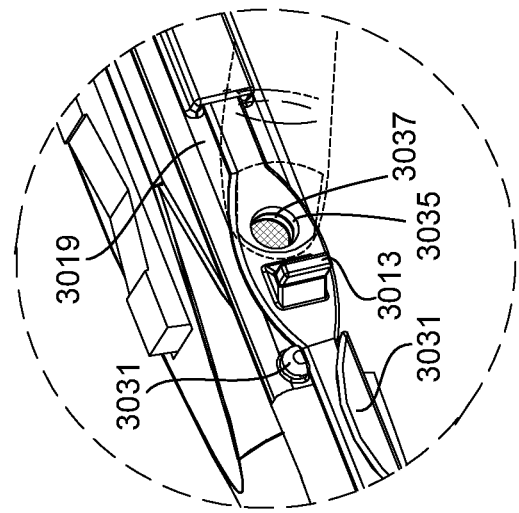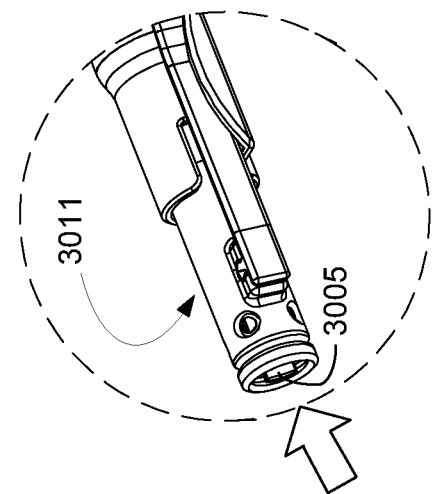
FIG. 3A

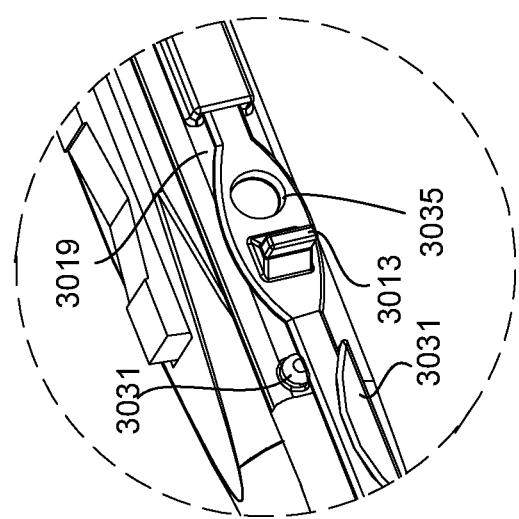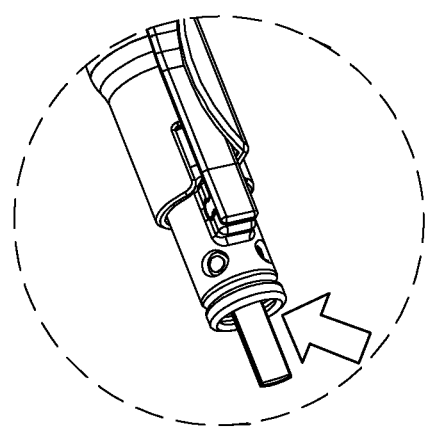
FIG. 3E

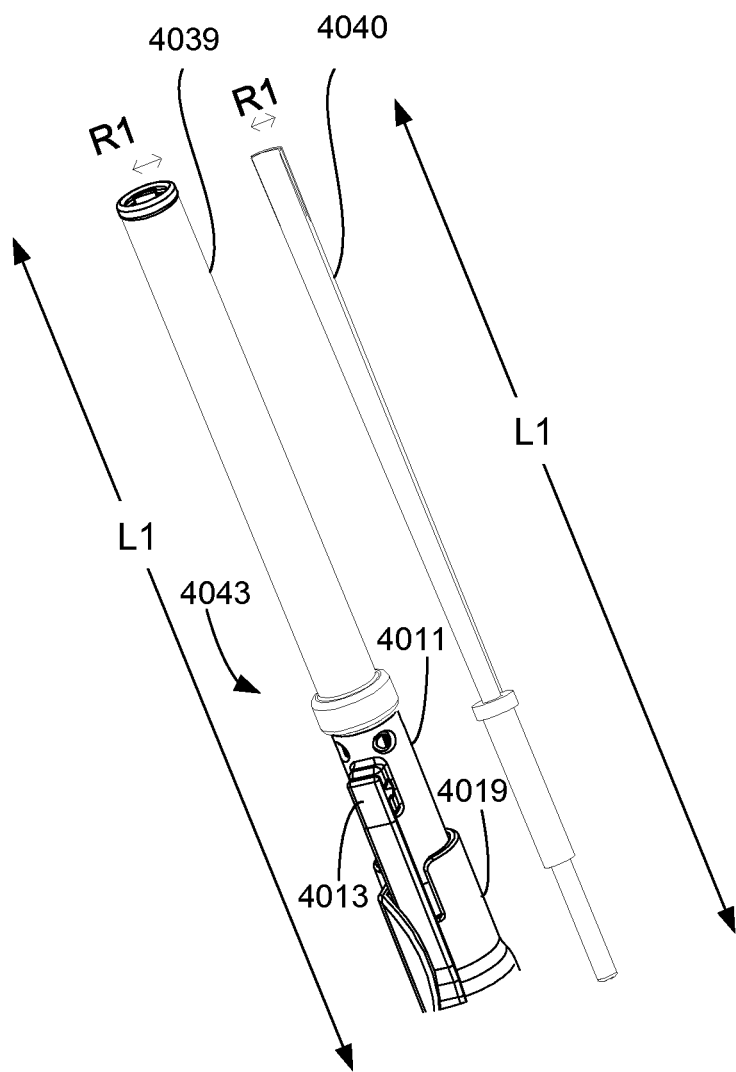

APPARATUS AND METHOD FOR ELECTROSURGICAL SUCTION

BACKGROUND OF THE INVENTION

1. Field of the Invention

The present invention relates to electrosurgery and, more particularly, to devices and methods for providing suction for electrosurgery.

2. Description of the Related Art

Many who are unfamiliar with modern surgical procedures may speak generally of "going under the knife" in anticipation of undergoing a surgical procedure. Such phrasing conjures a notion of a surgeon cutting into his patient using the blade of a scalpel. However, in general terms the true workhorse of surgeons today may be an electrical device, rather than a surgical scalpel.

Electrocautery devices may provide many advantages over traditional scalpels. In particular, electrocautery devices may help to control bleeding by cauterizing blood vessels while cutting. Despite such advantages, other challenges may still remain. A surgical smoke plume rising from a surgical site when electrocautery devices are in use may comprise steam as well as volatile organic compounds (including benzene, toluene, and xylene), acrolein, phenol, cresols, hydrogen cyanide, formaldehyde, acetaldehyde, polycyclic aromatic compounds, and carbon monoxide.

Exposure to some constituents of the surgical smoke plume may pose a health hazard to doctors and other operating room personnel. Thus there is a need for improved techniques for managing surgical smoke.

SUMMARY OF THE INVENTION

The invention pertains to techniques or processes for managing surgical smoke. In one embodiment a suction apparatus evacuates the surgical smoke. For example, the suction apparatus may be arranged adjacent to an electrocautery electrode, which may generate smoke during operation, for evacuating smoke from a surgical site.

The invention can be implemented in numerous ways, including as a method, system, device, or apparatus. Several embodiments of the invention are discussed below.

As a suction apparatus for an electrosurgical pencil that alternatively employs one of a plurality of differently shaped electrocautery electrodes, one embodiment of the invention can, for example, include at least an extendable suction tube comprising a main suction tube alternatively coupled with at least one of a plurality of differently shaped suction tip extension members, wherein each of the differently shaped suction tip extension members is shaped for receiving a corresponding respective one of the differently shaped electrocautery electrodes; a housing supportively coupled with the extendable suction tube; and an extension control slideably coupled with the housing and coupled with the extendable suction tube for controlling extendable movement of at least one of the differently shaped suction tip extension members over the corresponding respective one of the differently shaped electrocautery electrodes.

As a suction attachment for an electrosurgical pencil that alternatively employs one of a plurality of differently shaped electrocautery electrodes one embodiment of the invention can, for example, include at least a plurality of differently shaped suction tip extension members, wherein each of the differently shaped suction tip extension members is shaped for receiving a corresponding respective one of the differently shaped electrocautery electrodes; an attachment housing for fluid coupling with one of the plurality of differently shaped suction tip extension members; and an engagement member for releasably securing the suction attachment to the electrosurgical pencil.

As a method for using an electrosurgical pencil that alternatively employs one of a plurality of differently shaped electrocautery electrodes, one embodiment can, for example, include at least receiving one of the differently shaped electrocautery electrodes in a corresponding respective one of a plurality of differently shaped suction tip extension members of an extendable suction attachment; electrically activating the electrocautery electrode; and moveably extending one of the plurality of differently shaped suction tip extension members.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which:

FIG. 1A shows a suction apparatus for use with a surgical instrument.

FIGS. 1B and 1C are cutaway views of the suction apparatus shown in FIG. 1A.

FIGS. 2A-2E illustrate one-handed operation for controlled extension of the extendable suction tube of the extendable suction attachment.

FIGS. 3A-3E are detailed views illustrating operation of suction control ports.

FIGS. 4A-4C are detailed views illustrating a plurality of differently shaped suction tip extension members and a plurality of differently shaped electrocautery electrodes.

DETAILED DESCRIPTION OF EMBODIMENTS OF THE INVENTION

Figure 2C:
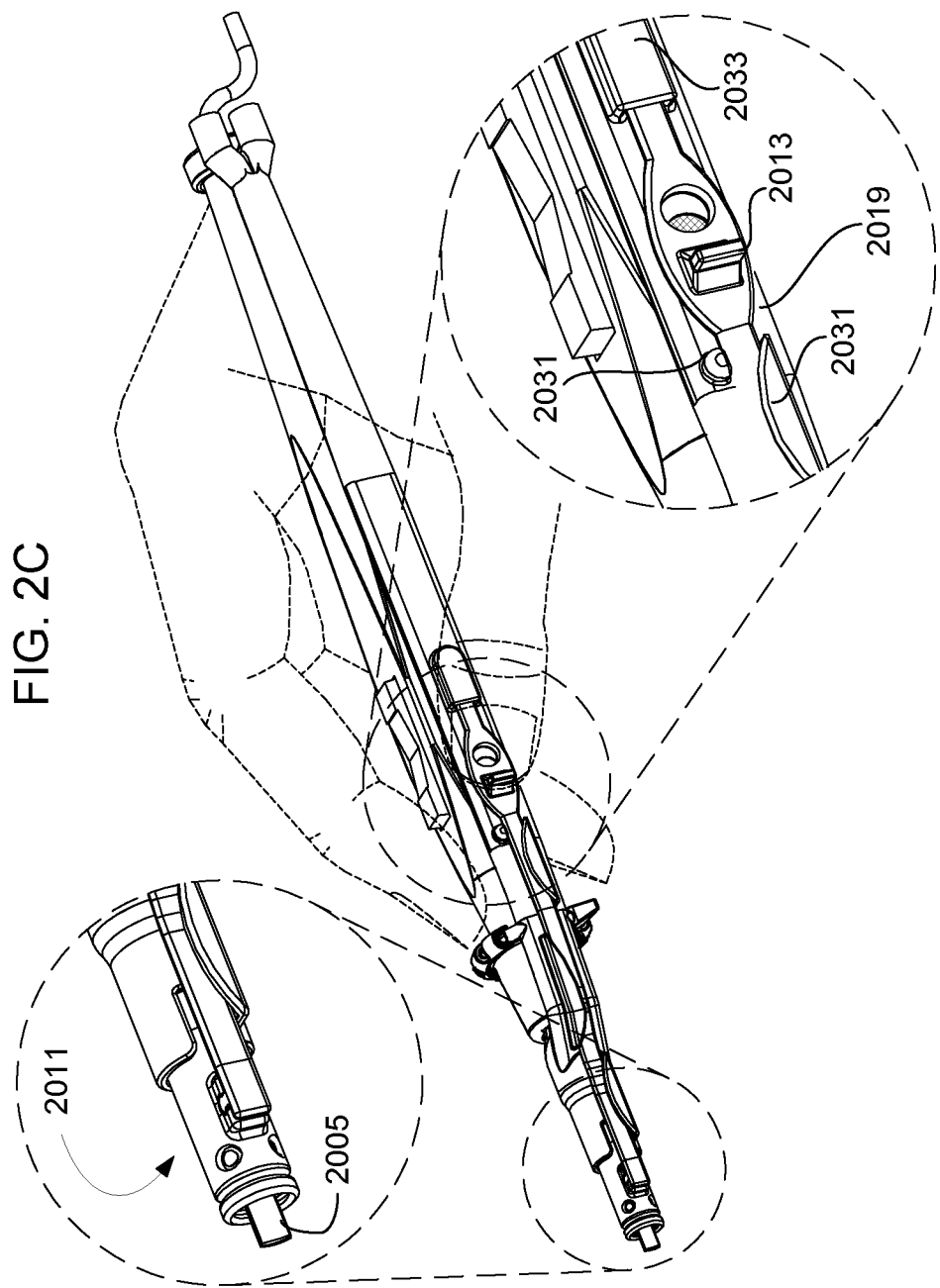

The invention pertains to techniques or processes for managing surgical smoke. In one embodiment a suction apparatus evacuates the surgical smoke. For example, the suction apparatus may be arranged adjacent to an electrocautery electrode, which may generate smoke during operation, for evacuating smoke from a surgical site.

Exemplary embodiments of the invention are discussed below with reference to FIGS. 1-12. However, those skilled in the art will readily appreciate that the detailed description given herein with respect to these figures is for explanatory purposes as the invention extends beyond these limited embodiments.

FIG. 1A shows a suction apparatus 1001 for use with a surgical instrument 1003 that may generate smoke. The suction apparatus 1001 may comprise an extendable suction attachment 1001 for one handed operation with the surgical instrument 1003. The suction apparatus 1001 (e.g. extendable suction attachment 1001) and its related components may be formed from one or more suitable materials, for example, comprising medical grade plastic. The suction apparatus 1001 (e.g. extendable suction attachment 1001) and its related components may be formed by suitable techniques, for example, by molding.

The surgical instrument 1003 may comprise an electrosurgical pencil 1003, which may have an electrocautery electrode 1005, a handpiece 1007, and at least one switch 1009 for activating the electrocautery electrode 1005. As shown in FIG. 1A, the electrocautery electrode 1005 may be coupled through switch 1009 and through a high voltage cable to a radio frequency generator 1010, which is suitably selected of electrosurgery.

Notwithstanding the foregoing, the invention is not strictly limited to use with the electrotrosurgical pencil 1003 and with the electrocautery electrode 1005 shown in the figures. In alternative embodiments, the surgical instrument may be other than the electrosurgical device. For example, the surgical instrument may be a laser surgical device or a radiosurgical device, which may generate smoke or other vaporous waste.

As shown in FIG. 1A, the extendable suction attachment 1001 may comprise an extendable suction tube 1011 having proximal and distal ends. The extendable suction tube 1011 may have a suction tube lumen 1012 arranged for receiving the electrocautery electrode 1005 of the electrosurgical pencil 1003. The suction apparatus 1001 may further comprise an extension control 1013 coupled with the extendable suction tube for controlling extendable movement of the distal end of the extendable suction tube 1011 over the electrocautery electrode 1005. For example, as shown in FIG. 1A, the extension control 1013 may comprise a thumb control 1013 coupled with the extendable suction tube 1011 for controlling extendable movement of the distal end of the extendable suction tube 1011 over the electrocautery electrode 1005. Switch 1009 may comprise a finger switch 1009 disposed on an outer surface of the handpiece 1007 of the electrosurgical pencil 1003; and the thumb control 1013 may be arranged as shown in FIG. 1A for one handed operation of the extendable suction attachment 1001 with the finger switch 1009 of the electrosurgical pencil.

As shown in FIG. 1A the extendable suction attachment 1001 may further comprise a smoke intake manifold 1014 having a smoke intake lumen, wherein the smoke intake manifold 1014 may be adapted for arrangement adjacent to the surgical instrument 1003 and/or the electrocautery electrode 1005. In particular, the smoke intake manifold 1014 may be arranged proximate to the electrocautery electrode 1005 when the electrocautery electrode 1005 is received by the suction tube lumen 1012 of the extendable suction tube 1011. As mentioned previously herein, in alternative embodiments the surgical instrument may be other than the electrosurgical device 1003 shown in FIG. 1A. For example, the surgical instrument may be the laser surgical device or the radiosurgical device. In such cases, the smoke intake manifold may be adapted for arrangement adjacent to the laser surgical device or the radiosurgical device.

As shown in FIG. 1A the smoke intake manifold 1014 may have an outer perimeter, and a plurality of suction intake ports 1017 may be arranged about the outer perimeter of the smoke intake manifold 1014 for evacuating smoke that may be generated by the surgical instrument 1003. The extendable suction attachment 1001 may further comprise an attachment housing 1019 fluidly coupled with the smoke intake manifold 1014 and with the proximal end of the extendable suction tube 1011.

The extendable suction tube 1011 may be adapted for evacuating and transporting liquid (or liquid intermixed with some smoke) during surgical operations with the surgical instrument 1003, while the smoke intake manifold 1014 may be adapted for evacuating and transporting smoke during surgical operations. The suction apparatus 1001 may further comprise and an isolation member disposed within the attachment housing 1019 for isolating the extendable suction tube 1011 and smoke intake manifold 1014 from fluid intercommunication within the attachment housing 1019. The isolation member disposed within the attachment housing 1019 may substantially isolate liquid evacuated by the extendable suction tube 1011 from smoke evacuated by the smoke intake manifold 1014. Further, the isolation member disposed within the attachment housing 1019 may provide for substantially separate transport of the liquid and smoke, so that the liquid may be output at a liquid output port 1023 of the suction apparatus 1001 for collection at a liquid vacuum and reservoir 1025, while the smoke may be output at a smoke output port 1027 of the suction apparatus 1001 for collection at a smoke vacuum and filter 1029. As shown in FIG. 1A, suitable tubing may be used for fluidly coupling the liquid output port 1023 of the suction apparatus 1001 with the liquid vacuum and reservoir 1025, and for fluidly coupling the smoke output port 1027 of the suction apparatus 1001 with the smoke vacuum and filter 1029. Since some smoke may be intermixed with the liquid, the liquid vacuum and reservoir 1025 may also include its own smoke filter.

FIGS. 1B and 1C are cutaway views of the suction apparatus 1001 shown in FIG. 1A. In particular, FIG. 1C shows a detailed cutaway view. As shown in FIGS. 1B and 1C, the attachment housing 1019 may be supportively coupled with the proximal end of the extendable suction tube 1011.

As shown in FIGS. 1B and 1C, the extendable suction tube 1011 may be adapted for evacuating and transporting liquid (or liquid intermixed with some smoke) during surgical operations with the surgical instrument 1003. In FIGS. 1B and 1C notional flat arrowheads show the flow of the liquid from intake at the distal end of the extendable suction tube 1011, through the lumen 1012 of the extendable suction tube 1011, and through a first interior chamber 1018 of the attachment housing 1019 to be output at the liquid output port 1023 of the suction apparatus 1001.

The smoke intake manifold 1014 may be adapted for evacuating and transporting smoke during surgical operations. In FIGS. 1B and 1C notional flat arrowheads show the flow of smoke from the intake manifold, through a second interior chamber 1020 of the attachment housing 1019 to be output at the smoke output port 1027 of the suction apparatus 1001. The isolation member 1021 is shown in FIG. 1C separating the first and second interior chambers 1018, 1020.

As shown in FIG. 1C, the isolation member 1021 may be disposed within the attachment housing 1019 for isolating the extendable suction tube 1011 and smoke intake manifold 1014 from fluid intercommunication within the attachment housing 1019. As shown in FIG. 1C, the isolation member 1021 may substantially isolate liquid evacuated by the extendable suction tube 1011 from smoke evacuated by the smoke intake manifold 1014. The isolation member 1021 may coupled with the extendable suction tube 1011 and the smoke intake manifold 1014 for substantially isolating the extendable suction tube 1011 and smoke intake manifold 1014 from fluid intercommunication.

FIGS. 2A-2E illustrate one-handed operation for controlled extension of the extendable suction tube 2011 of the extendable suction attachment 2001. In the figures, an operators hand, and in particular movement of the operator's thumb is shown in dashed or phantom line. Extension control 2013 (for example thumb control 2013) may be slideably coupled with the attachment housing 2019 and may be coupled with the extendable suction tube 2011 for controlling extendable movement of the distal end of the extendable suction tube 2011 over the electrocautery electrode 2005. Accordingly, as shown in FIGS. 2A-2E, the operator's thumb may slideably move thumb control 2013 for controlling extendable movement of the distal end of the extendable suction tube 2011 over the electrocautery electrode 2005.

As will be discussed in greater detail subsequently herein with respect to FIGS. 2A-2E, the extendable suction attachment 2001 may further comprise: a first movement limiting slot 2031 coupled with the attachment housing 2019 for limiting movement of the extendable suction tube 2011 to a preselected full extent of the distal end covering the electrocautery electrode; and an opposing movement limiting slot 2033 coupled with the attachment housing for limiting movement of the extendable suction tube 2011 to a preselected retraction extent of the distal end of the extendable suction tube 2011, so as to expose the electrocautery electrode outside 2005 of the lumen of the extendable suction tube 2011.

FIG. 2A shows movement of the extendable suction tube 2011 to a position of a preselected full extent of the distal end of the extendable suction tube 2011 covering the electrocautery electrode 2005. As shown in FIG. 2A the first movement limiting slot 2031 may be coupled with the attachment housing 2019 for limiting movement of the extendable suction tube 2011 (via limiting movement of the thumb control 2013) to the preselected full extent of the distal end covering the electrocautery electrode 2005. FIG. 2B is a detailed cutaway view showing the first movement limiting slot 2031 limiting the movement of the extendable suction tube (via limiting movement of the thumb control 2013) to the preselected full extent of the distal end covering the electrocautery electrode.

FIG. 2C shows movement of the extendable suction tube 2011 to a position of an intermediate extent of the distal end of the extendable suction tube 2011 partially retracted and partially covering the electrocautery electrode 2005.

FIG. 2D shows movement of the extendable suction tube 2011 to a position of a preselected retraction extent of the distal end of the extendable suction tube 2011, so as to expose the electrocautery electrode 2005 outside of the lumen of the extendable suction tube 2011. FIG. 2E is a detailed cutaway view showing the opposing movement limiting slot 2033 limiting the movement of the extendable suction tube (via limiting movement of the thumb control 2013) to the preselected retraction extent of the distal end of the extendable suction tube, so as to expose the electrocautery electrode outside of the lumen of the extendable suction tube.

FIGS. 3A-3E are detailed views illustrating operation of suction control ports, which may be fluidly coupled with the proximate end of the extendable suction tube 3011 for controlling suction at the distal end of the extendable suction tube 3011. As shown in FIGS. 3A-3E, a first suction control port 3035 may be disposed at a location extending through the thumb control 3013. A second suction control port 3037 may extend through a wall of the attachment housing 3019, wherein the second suction control port 3037 may be fluidly coupled with the proximate end of the extendable suction tube 3011 for controlling suction at the distal end of the extendable suction tube 3011. As shown in FIGS. 3A-3E, the second suction control port 3037 may be arranged at a location adjacent to the location of the first suction control port 3037.

Figure 3B:
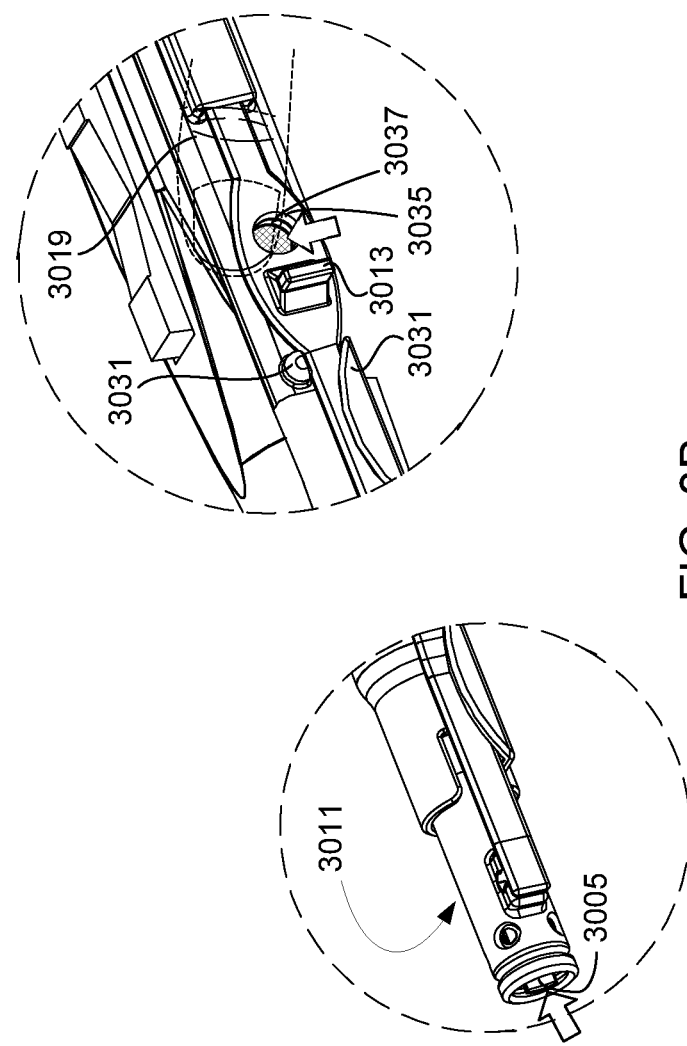
Figure 3C:
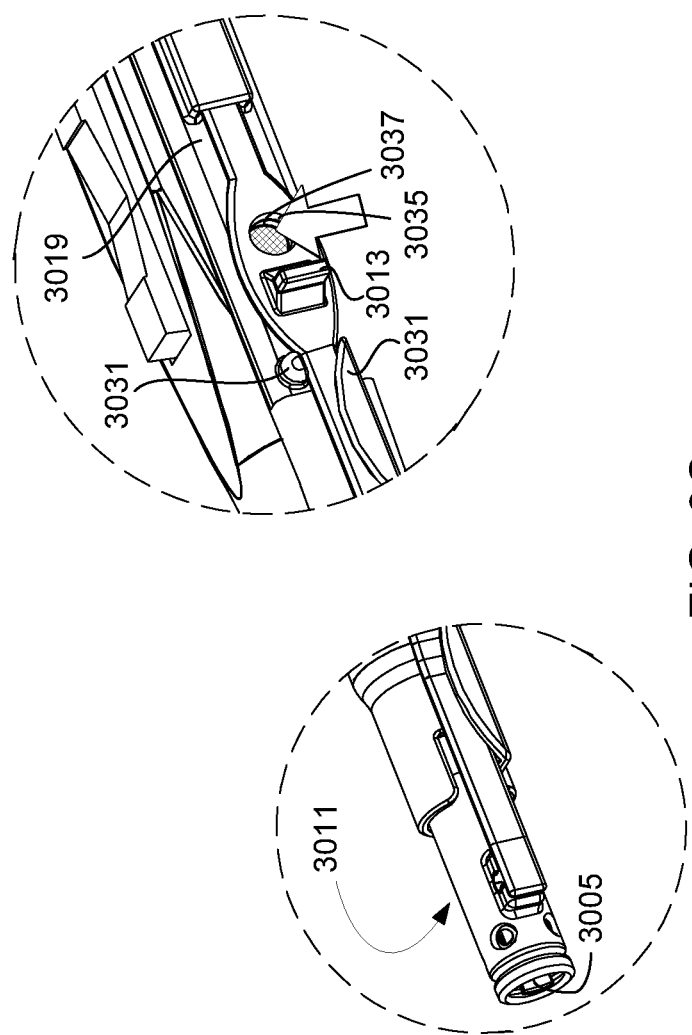

As shown in FIGS. 3A-3C, the first movement limiting slot 3031 may be coupled with the attachment housing 3019 for limiting movement of the extendable suction tube 3011 to the preselected full extent of the distal end of the extendable suction tube 3011 covering the electrocautery electrode 3005. In such case, first and second suction control ports 3035, 3037 may be arranged in substantial alignment as shown in FIGS. 3A-3C, when the thumb control 3013 slideably coupled with the attachment housing 3019 controls the movement of the extendable suction tube 3011 to the preselected full extent of the distal end of the suction tube 3011 covering the electrocautery electrode 3005.

As shown in FIG. 3A, the first suction control port 3035 may be disposed at a location extending through the thumb control 3013, and substantially sized for variable sealing of the first suction control port by an operator's thumb in one handed operation of the extended suction attachment with the electrosurgical pencil. In the figures, the operator's thumb is drawn in dashed of phantom line. Full sealing by the operator's thumb in FIG. 3A is shown corresponding to full suction at the distal end of the suction tube 3011, wherein such full suction at the distal end of the suction tube 3011 is depicted in FIG. 3A by a notional flat arrow head.

Partial sealing by the operator's thumb in FIG. 3B is shown corresponding to diminished suction at the distal end of the suction tube 3011, wherein such diminished suction at the distal end of the suction tube 3011 is depicted in FIG. 3B by a notional flat arrow head having a reduced size. Parasitic control suction may be admitted to the control ports 3035, 3037 by the partial sealing by the operator's thumb in FIG. 3B, wherein such parasitic control suction is depicted in FIG. 3B by another notional flat arrow head having the reduced size.

No sealing of control ports 3035, 3037 by any operator's thumb is shown in FIG. 3C. Accordingly, substantially no suction is shown in FIG. 3C at the distal end of the suction tube 3011, and full parasitic control suction may be admitted to the control ports 3035, 3037, wherein such full parasitic control suction is depicted in FIG. 3C by a full sized notional flat arrow head at the control ports 3035, 3037.

Figure 3D:
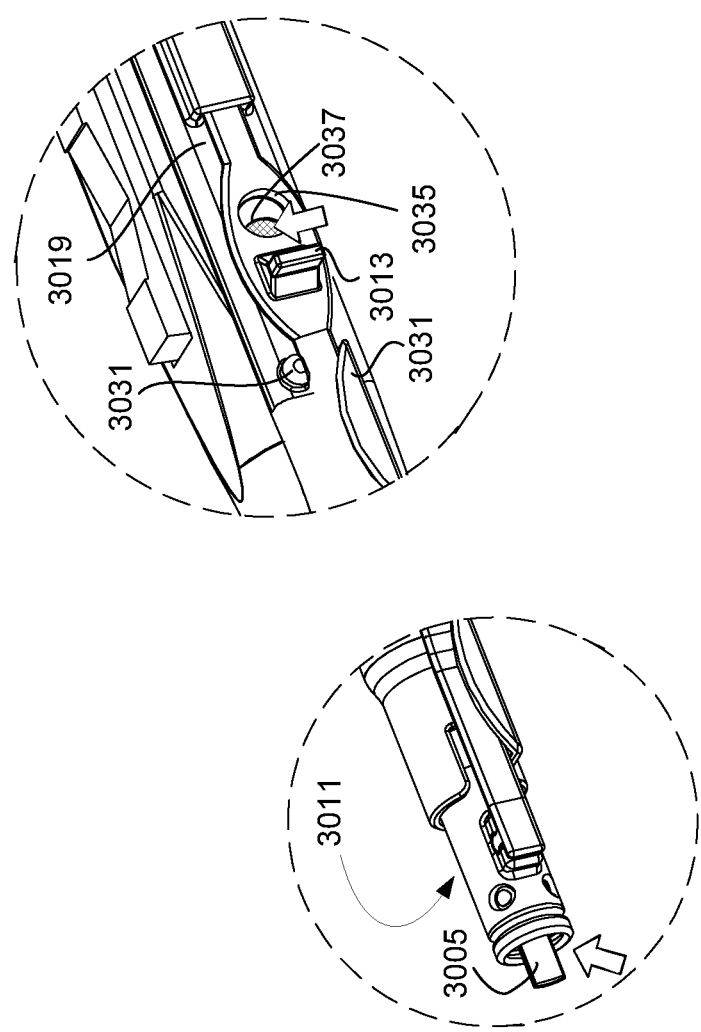

In contrast to FIGS. 3A-3C, which show that the first and second suction control ports 3035, 3037 may be in substantial alignment when the thumb control 3013 slideably coupled with the attachment housing 3019 controls the movement of the extendable suction tube 3011 to the preselected full extent of the distal end of the suction tube 3011 covering the electrocautery electrode 3005; as shown in FIGS. 3D-3E variable mis-alignment the first and second control ports 3035, 3037 may provide variable sealing of the control ports 3035 for controlling suction at the distal end of suction tube 3011. FIG. 3D shows the first and second suction control ports 3035, 3037 in substantial mis-alignment when the thumb control 3013 slideably coupled with the attachment housing 3019 controls the movement of the extendable suction tube 3011 to the position of intermediate extent of the distal end of the extendable suction tube 3011 partially retracted and partially covering the electrocautery electrode 3005. Partial sealing by partial or intermediate mis-alignment of the first and second control ports 3035, 3037 in FIG. 3D is shown as corresponding to diminished suction at the distal end of the suction tube 3011, wherein such diminished suction at the distal end of the suction tube 3011 is depicted in FIG. 3D by a notional flat arrow head having a reduced size. Some parasitic control suction may be admitted to the control ports 3035, 3037 by the partial sealing by partial or intermediate mis-alignment of the first and second control ports 3035, 3037, wherein such parasitic control suction is depicted in FIG. 3D by another notional flat arrow head having the reduced size.

FIG. 3E shows movement of the extendable suction tube 3011 to the position of preselected retraction extent of the distal end of the extendable suction tube 3011, so as to expose the electrocautery electrode 3005 outside of the lumen of the extendable suction tube 3011. In substantially full mis-alignment as shown in FIG. 3E, the second suction control port may no longer be visible through the first suction control port 3035. A substantially full sealing by the substantially full mis-alignment of the first and second control ports in FIG. 3E is shown as corresponding to substantially full suction at the distal end of the suction tube 3011, wherein such substantially full suction at the distal end of the suction tube 3011 is depicted in FIG. 3E by the full size notional flat arrow head.

Figure 4B:
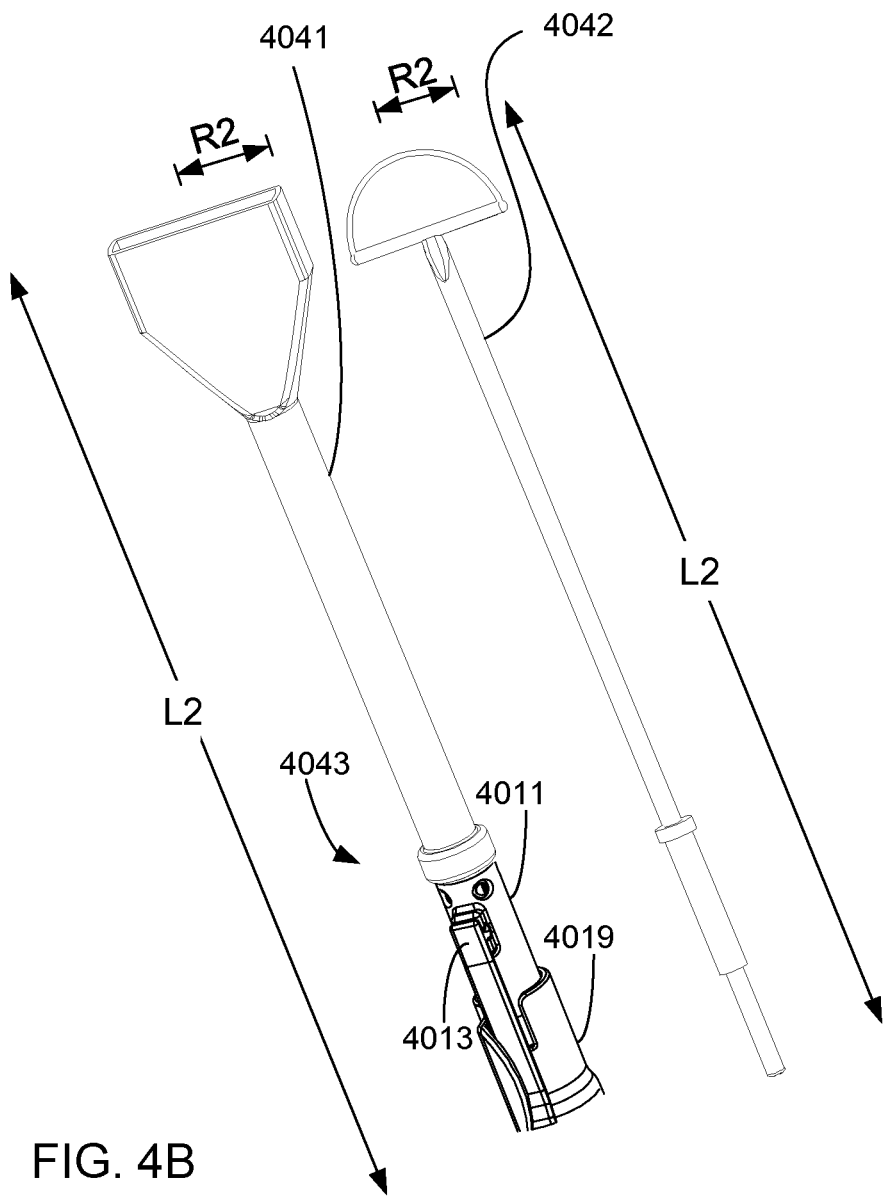
Figure 4C:
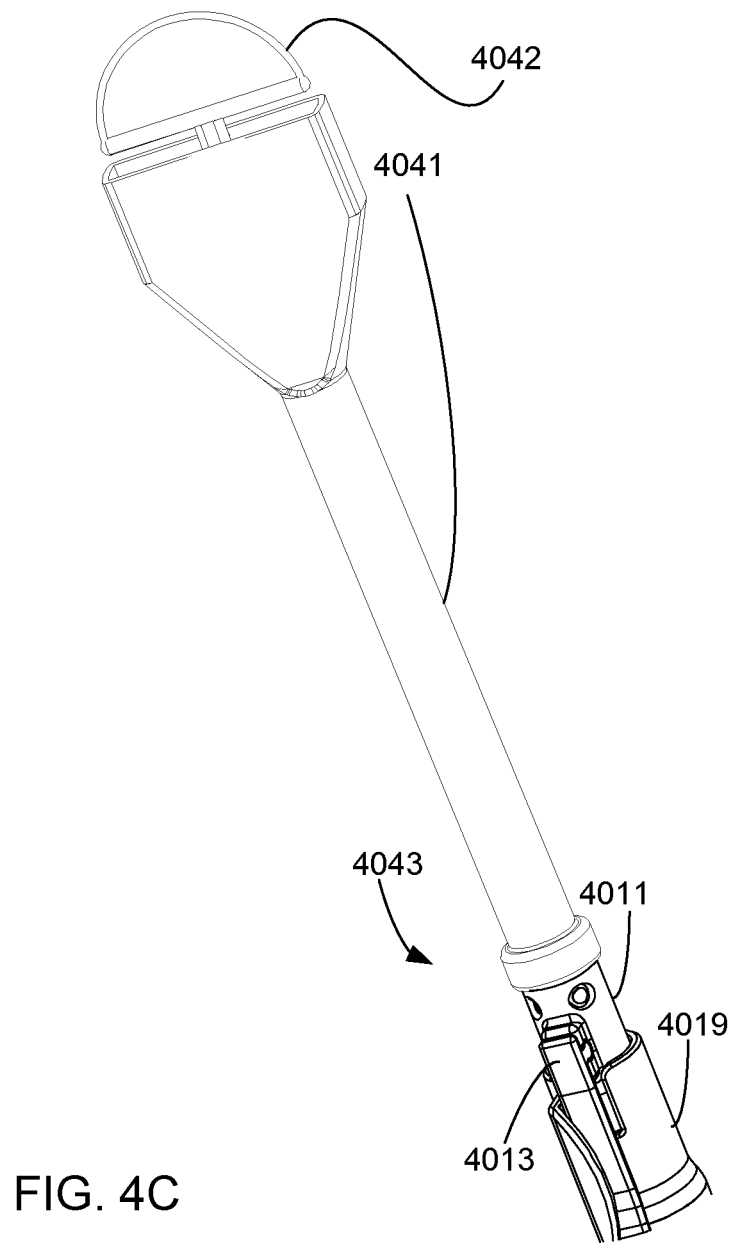

FIGS. 4A-4C are detailed views illustrating a plurality of differently shaped suction tip extension members and a plurality of differently shaped electrocautery electrodes. The suction apparatus may be used with the electrosurgical pencil, which may alternatively employ one of the plurality of differently shaped electrocautery electrodes 4040, 4042. As shown in FIGS. 4A-4C extendable suction tube 4043 may comprise main suction tube 4011 alternatively coupled with at least one of a plurality of differently shaped suction tip extension members 4039, 4041, wherein each of the differently shaped suction tip extension members 4039, 4041 is shaped for receiving a corresponding respective one of the differently shaped electrocautery electrodes 4040, 4042. Attachment housing 4019 may be supportively coupled with the extendable suction tube 4043. Extension control 4013 may be slideably coupled with the housing 4019 and coupled with extendable suction tube 4043 for controlling extendable movement. Accordingly, extendable movement of at least one of the differently shaped suction tip extension members 4039, 4041 may be controlled over the corresponding respective one of the differently shaped electrocautery electrodes 4040, 4042.

As discussed in detail previously herein, the first movement limiting slot may be coupled with the housing for limiting movement of extendable suction tube to the preselected full extent over the electrocautery electrode. The opposing movement limiting slot may be coupled with the housing for limiting movement of the extendable suction tube to the preselected retraction extent over the electrocautery electrode, so as to expose the electrocautery electrode outside of the extendable suction tube. Further in line with such previous teachings herein, first movement limiting slot may be coupled with the housing for limiting movement of at least one of the differently shaped suction tip extension members 4039, 4041 to a preselected full extent over the corresponding respective one of the differently shaped electrocautery electrodes 4040, 4042. Opposing movement limiting slot may be coupled with the housing for limiting movement of at least one of the differently shaped suction tip extension members 4039 to the preselected retraction extent over the corresponding respective one of the differently shaped electrocautery electrodes 4040, 4042, so as to expose the corresponding respective one of the differently shaped electrocautery electrodes 4040, 402 outside of at least one of the differently shaped suction tip extension members 4039, 4041.

As shown in FIGS. 4A-4C, each of the suction tip extension members 4039, 4041 may have a respective one of a plurality of differently shaped lumens, so that each of the lumens may be shaped for receiving the corresponding respective one of the differently shaped electrocautery electrodes 4040, 4042. Each of the suction tip extension members 4039, 4041 may have a respective one of a plurality of different longitudinal dimensions L1, L2, so that each of the longitudinal dimensions L1, L2 of the suction tip extension members may be selected for receiving the corresponding respective one of the differently shaped electrocautery electrodes 4040, 4042. Each of the suction tip extension members 4039, 4041 may have a respective one of a plurality of different radial dimensions R1, R2, so that each of the radial dimensions R1, R2 of the suction tip extension members 4039, 4041 may be selected for receiving the corresponding respective one of the differently shaped electrocautery electrodes 4040, 4042.

For example, as shown in FIG. 4A a first suction tip extension member 4039 may have a first longitudinal dimension L1 selected for receiving a blade shaped electrocautery electrode 4040 having a corresponding longitudinal dimension L1. The first suction tip extension member 4039 may have a first radial dimension R1 selected for receiving the blade shaped electrocautery electrode 4040 having a corresponding radial dimension R1.

As another example, as shown in FIG. 4B a second suction tip extension member 4041 may have a longitudinal dimension L2 selected for receiving a hoop shaped electrocautery electrode 4042 having corresponding longitudinal dimension L2. The second suction tip extension member 4041 may have a radial dimension R2 selected for receiving the hoop shaped electrocautery electrode 4042 having corresponding radial dimension R2. Comparison of FIGS. 4B and 4C illustrates movement between alternative extension and retraction positions of the extendable suction tube 4043 over the hoop shaped electrocautery electrode 4042.

Figure 4D:
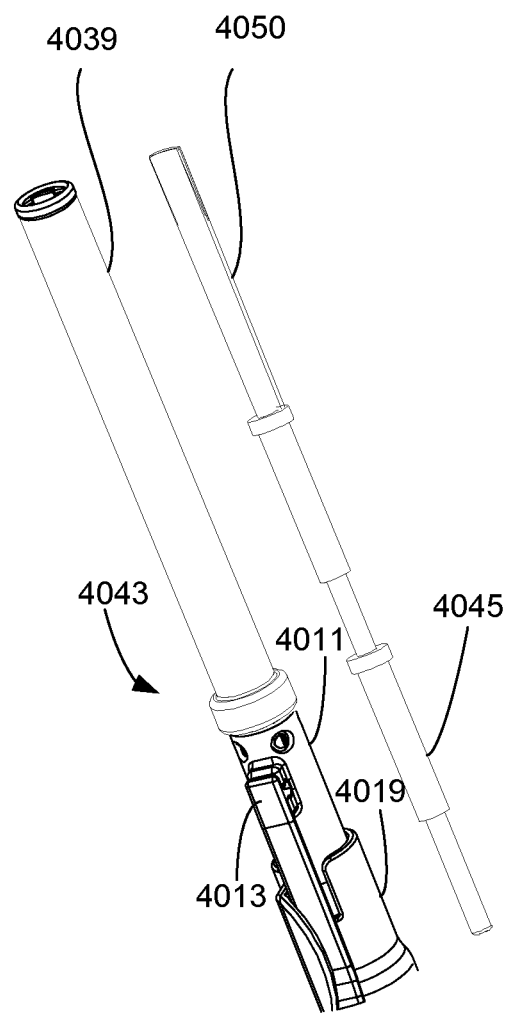
FIGS. 4D-4E are detailed views illustrating an electrode extender, a plurality of differently shaped suction tip extension members and a plurality of differently shaped electrocautery electrodes.
Figure 4E:
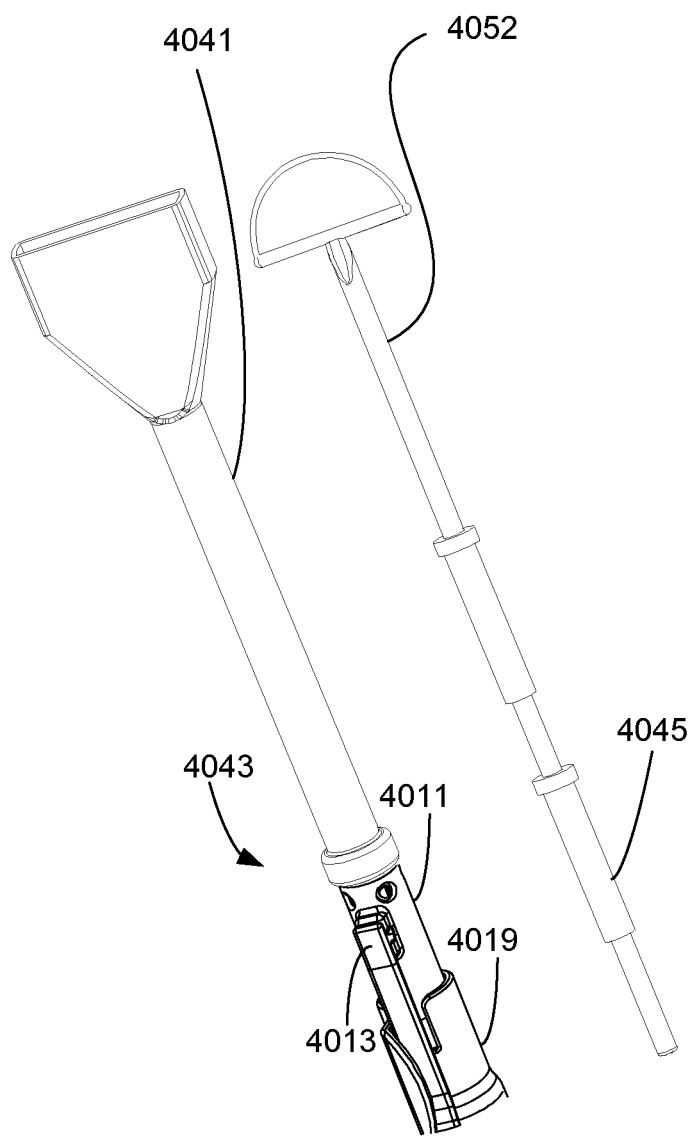

FIGS. 4D-4E are detailed views illustrating an electrode extender 4045, a plurality of differently shaped suction tip extension members 4039, 4041 and a plurality of differently shaped electrocautery electrodes 4050, 4052. Accordingly the suction apparatus may be adapted for receiving at least one electrode extender 4045 for alternatively coupling with one of the plurality of differently shaped electrocautery electrodes 4050, 4052. At least one of the suction tip extension members 4039, 4041 may be adapted for receiving at least one electrode extender 4045 for alternatively coupling with one of the plurality of differently shaped electrocautery electrodes 4050, 4052.

Figure 5A:
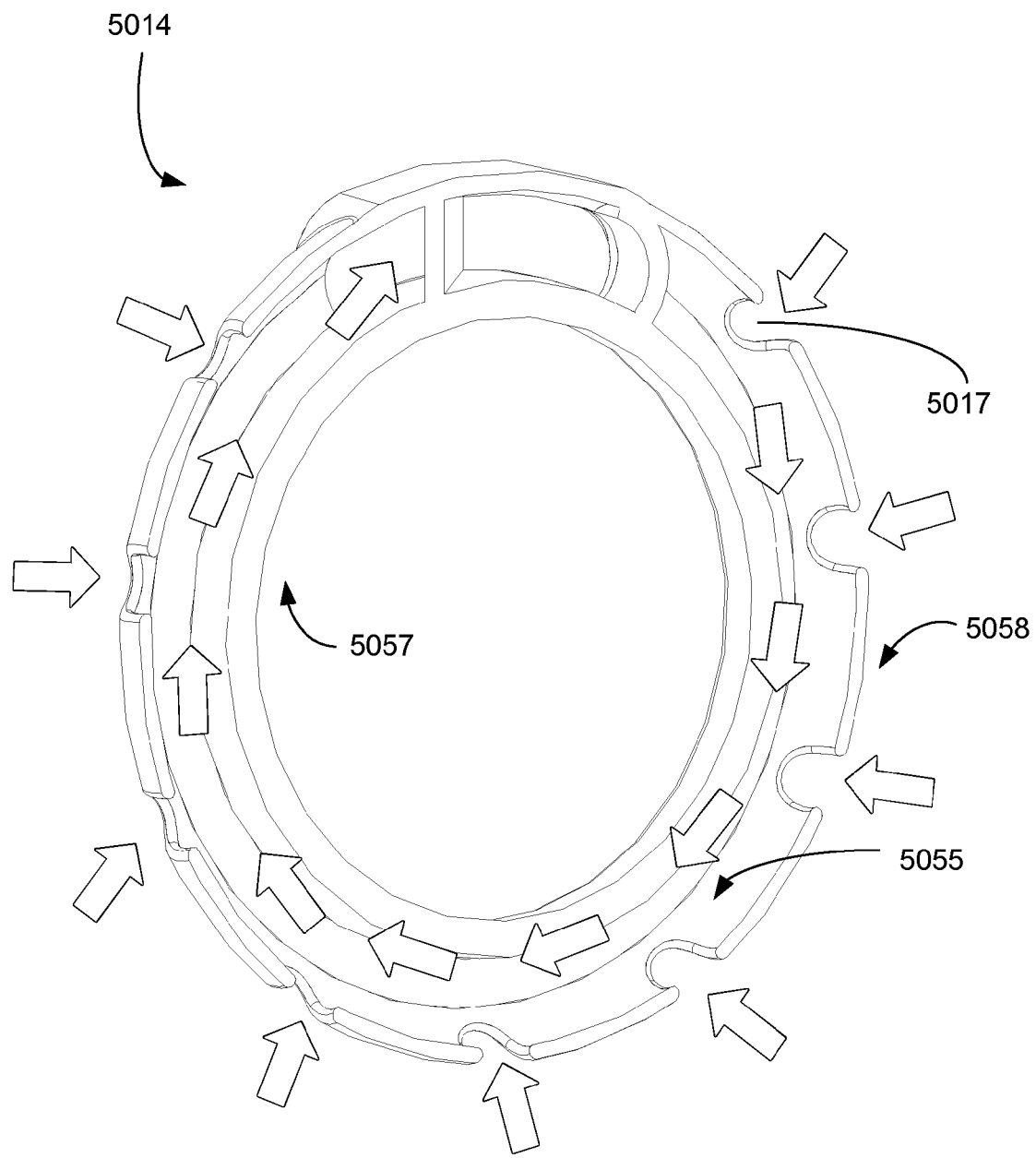
FIG. 5A is a detailed cutaway view of one embodiment of the smoke intake manifold of the suction apparatus.

FIG. 5A is a detailed cutaway view of one embodiment of the smoke intake manifold of the suction apparatus. The smoke intake manifold may comprise a ring manifold 5014, which may have a lumen 5055 extending substantially around the ring manifold 5014. The ring manifold 5014 may have an inner perimeter 5057 for receiving the surgical instrument, and may have an outer perimeter 5058. A plurality of suction intake ports 5017 may be arranged about the outer perimeter 5058 of the ring manifold 5014 for evacuating smoke that may be generated by the surgical instrument. In FIG. 5A, notional flat arrowheads show smoke taken into the lumen 5055 of the ring manifold 5014 through the suction intake ports. As shown by notional flat arrowheads in FIG. 5A, the smoke may move through the lumen 5055 of the ring manifold 5014 to be collected in one of the interior chambers of the attachment housing.

Figure 5B:
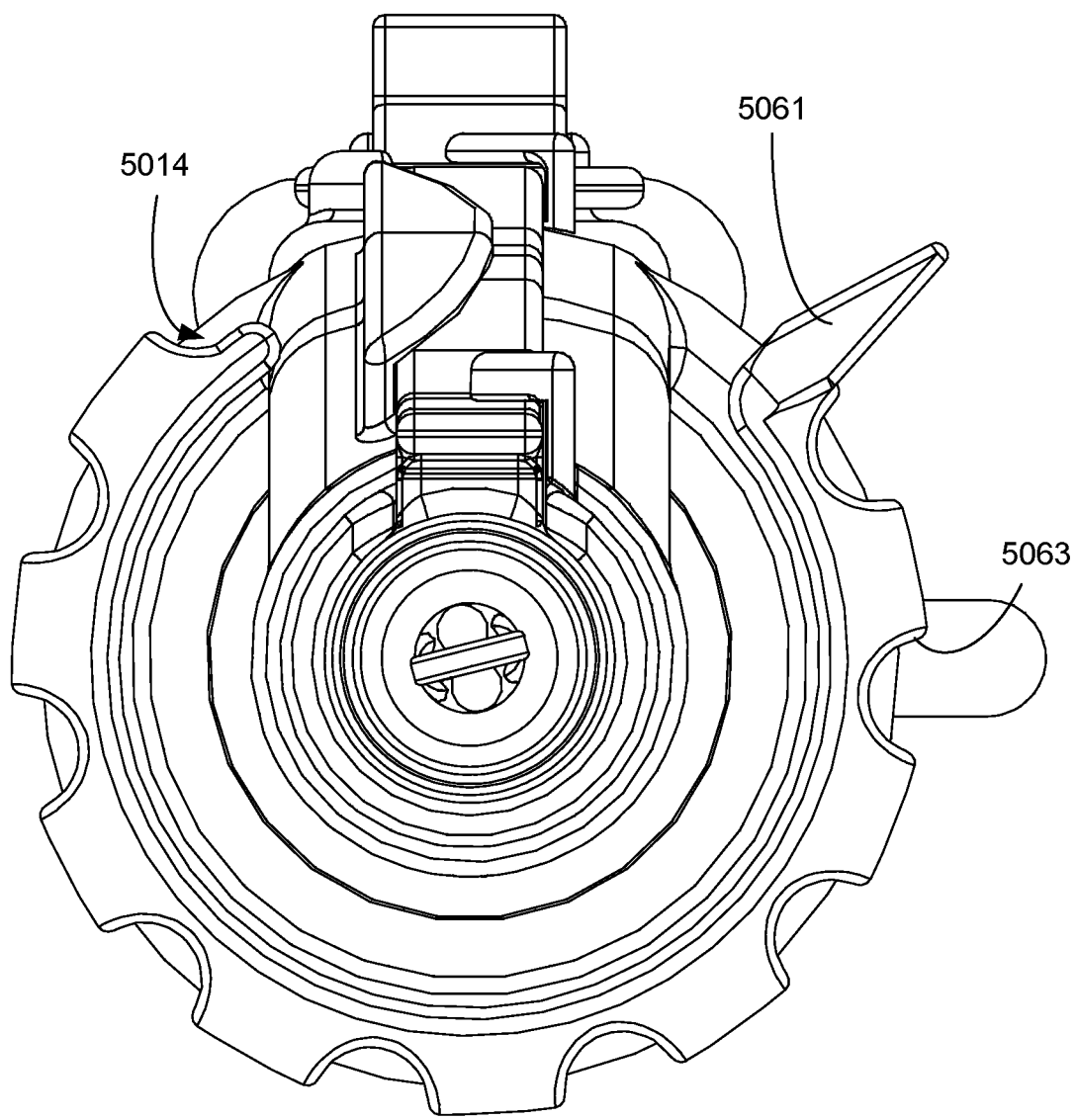
FIGS. 5B-5D are end views showing controllable operation of the smoke intake manifold of the suction apparatus.
Figure 5C:
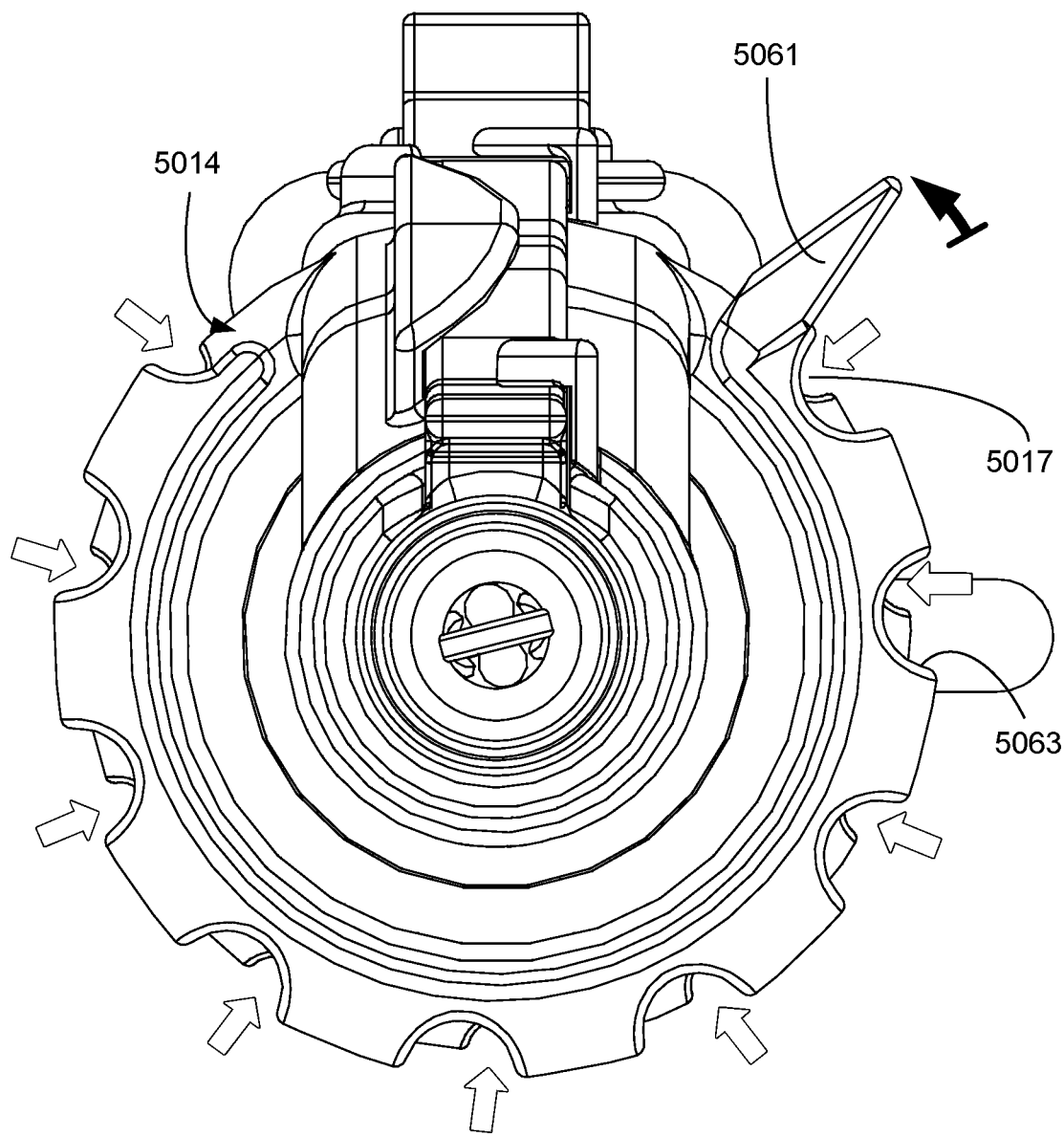
Figure 5D:
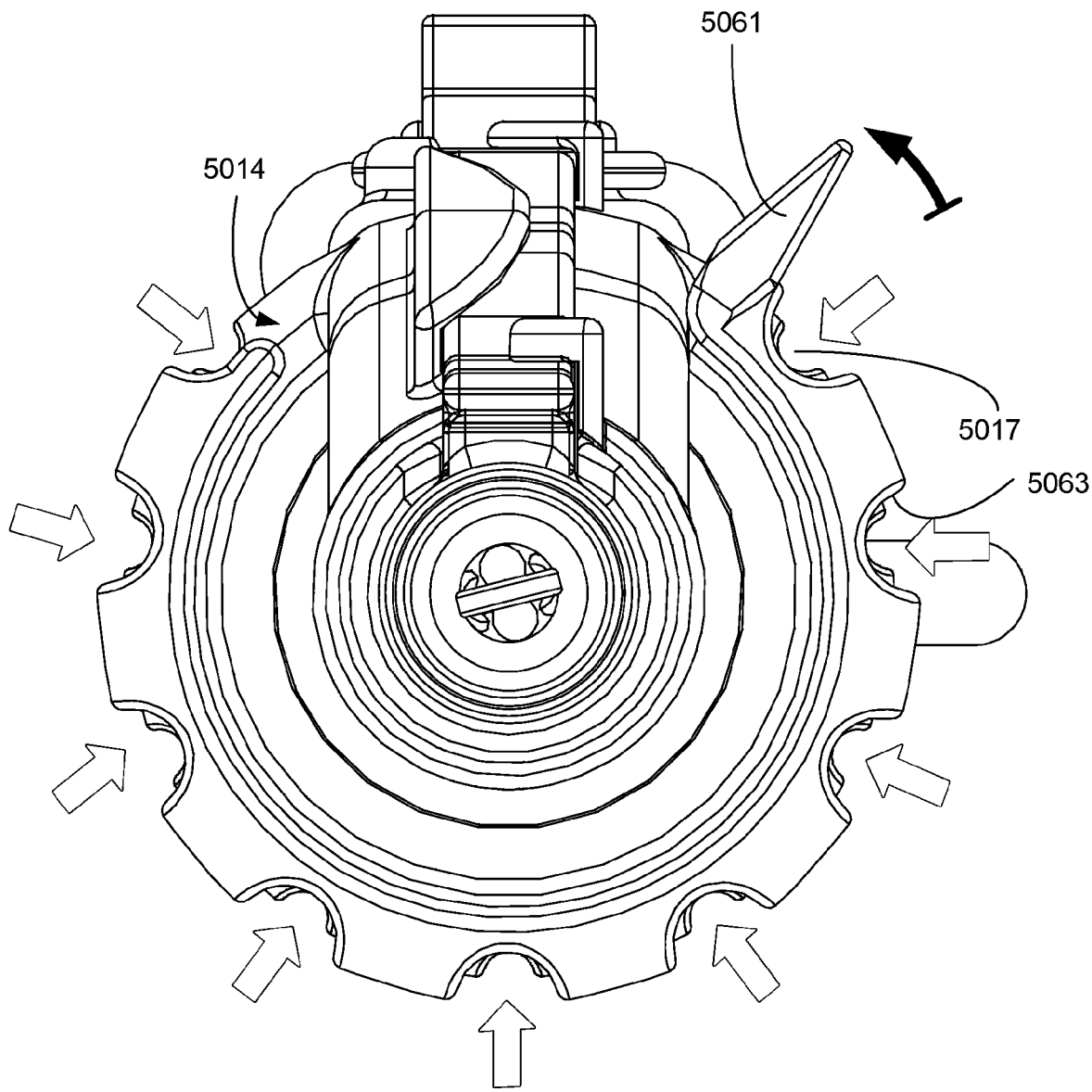

FIGS. 5B-5D are end views showing controllable operation of the smoke intake manifold (e.g. ring manifold 5014) of the suction apparatus. The suction apparatus may further comprise a rotatable suction control band 5061, which may substantially encircle the suction intake ports 5017 of the outer perimeter of the ring manifold 5014 for variably sealing the suction intake ports 5017 of the ring manifold 5014, so as to variably control suction for evacuating smoke that may be generated by the surgical instrument. As shown in FIGS. 5B-5D the rotatable suction control band 5061 may have a plurality of suction control ports 5063 penetrating the rotatable suction control band 5061. Each of the suction control ports 5063 may be arranged adjacent to a respective one of the suction intake ports 5017 for variable alignment therewith, so as to variably control suction for evacuating smoke that may be generated by the surgical instrument.

For example, as shown in FIG. 5B, the rotatable suction control band 5061 may be rotatably positioned for substantially sealing the suction intake ports of the ring manifold 5014. In FIG. 5B, the plurality of suction control ports 5063 may be fully mis-aligned with the suction intake ports, so that the suction intake ports are not visible.

As another example, as shown in FIG. 5C, the rotatable suction control band 5061 may be rotatably positioned for partial sealing of the suction intake ports 5017 of the ring manifold 5014, so as to provide for partial admittance of smoke into the suction intake ports 5017 of the ring manifold 5014. In FIG. 5C, small flat notional arrowheads illustrate the partial admittance of smoke. In FIG. 5C, the plurality of suction control ports 5063 may be partially aligned and may be partially mis-aligned with the suction intake ports 5017, so that the suction intake ports 5017 are partially visible.

As yet another example, as shown in FIG. 5D, the rotatable suction control band 5061 may be rotatably positioned for substantially open admittance of smoke at the suction intake ports 5017 of the ring manifold 5014. In FIG. 5D, large flat notional arrowheads illustrate the substantially open admittance of smoke. In FIG. 5D, the plurality of suction control ports 5063 may be fully aligned with the suction intake ports 5017, so that the suction intake ports 5017 are fully visible.

Figures 6A, 6B:
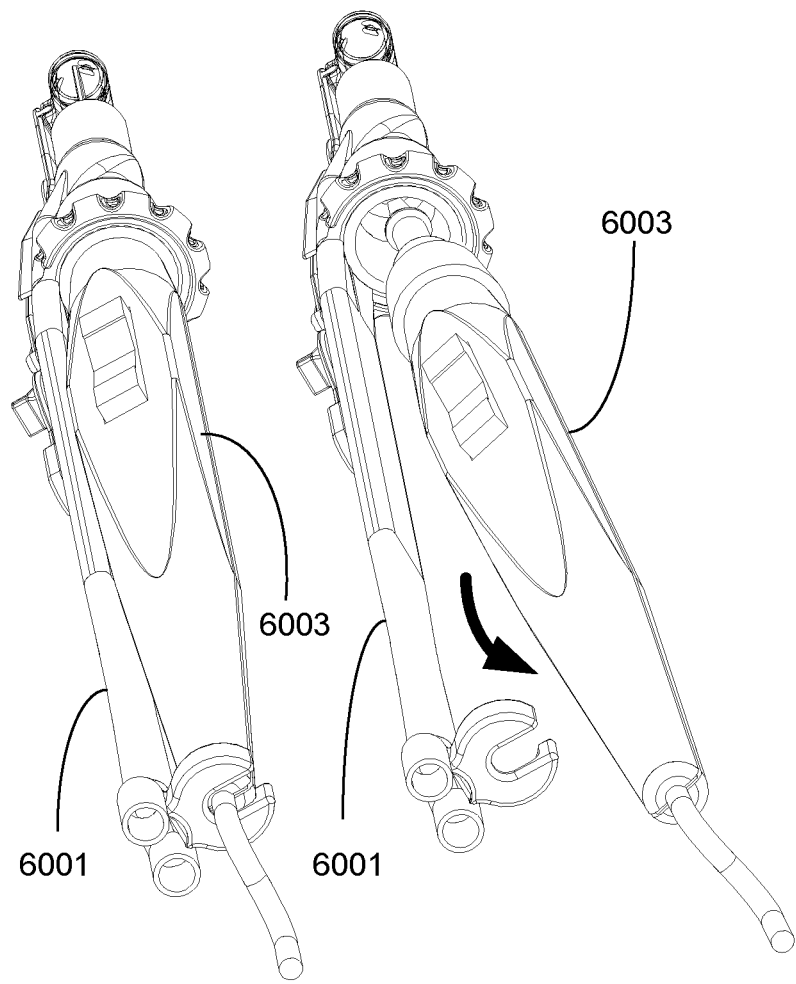
FIGS. 6A-6E illustrate engagement and releasable securing of the suction attachment with the surgical instrument.

FIGS. 6A-6E illustrate engagement and releasable securing of the suction attachment 6001 with the surgical instrument 6003 (e.g. electrosurgical pencil 6003). For example, FIG. 6A illustrates the suction attachment releasably secured to the surgical instrument 6003. FIG. 6B show partial separation of the suction attachment 6001 and the surgical instrument 6003, as the surgical instrument 6003 is lifted back and away from the suction attachment 6001.

Figure 6C:
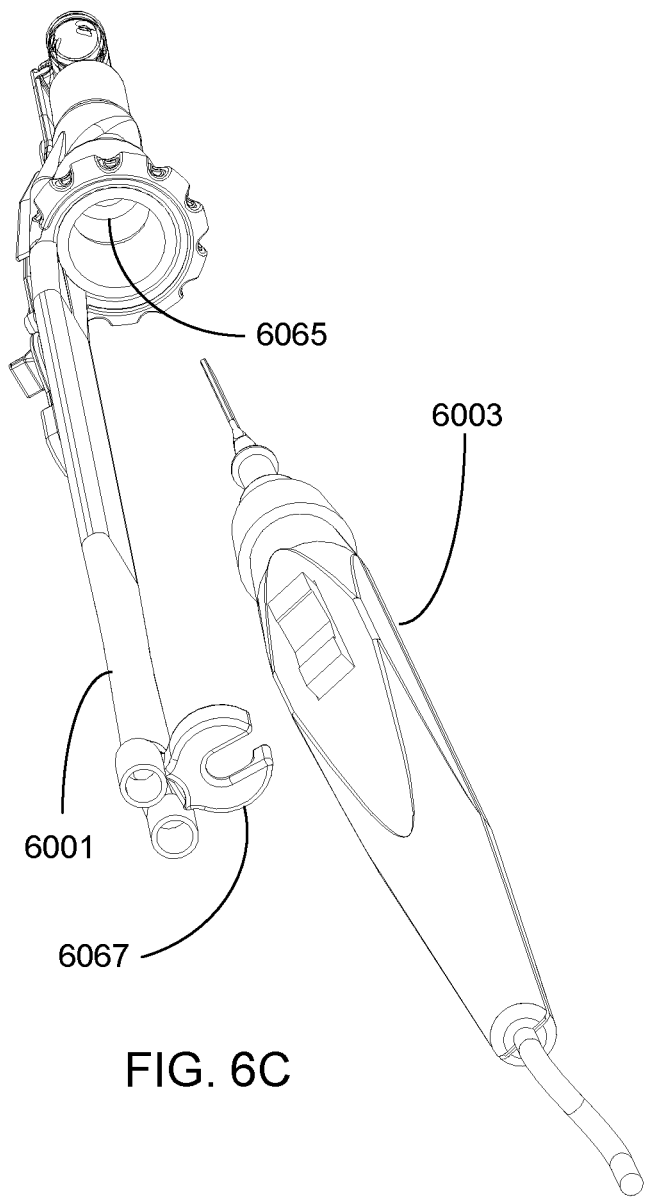

FIG. 6C shows full separation of the suction attachment 6001 from the surgical instrument 6003. As shown, the suction attachment 6001 may be separable from the surgical instrument 6003. The suction attachment may be disposable.

At such full separation, a first engagement member 6065 may be visible. As shown in FIG. 6C, the first engagement member 6065 may be coupled at a location within a central bore of the suction attachment 6001 for receiving and releasably securing the surgical instrument. The first engagement 0member 6065 may comprise an o-ring. The first engagement member 6065 may comprise an expanded foam. The first engagement member 6065 may comprise an adhesive tape. The first engagement member 6065 may comprise a thermoelastic polymer gasket.

As shown in FIG. 6C, an opposing engagement member 6067 may be coupled at a distal location from first engagement member 6065, for receiving and releasably securing the surgical instrument. The opposing engagement member 6067 may comprise a U shaped clip. The opposing engagement member may be made integral with the attachment housing of the suction attachment 6001.

Figures 6D, 6E:
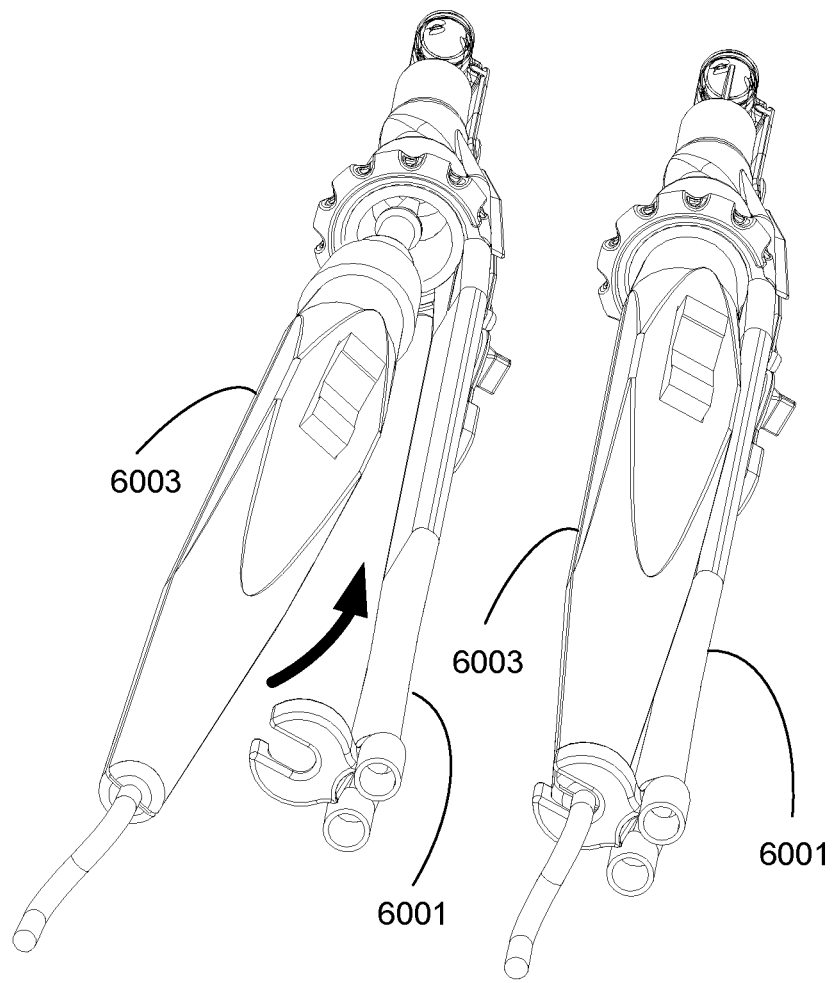

The engagement members of the suction attachment 6001 may be alternatively arrangeable with the electrosurgical pencil for ambidextrous one handed operation of the thumb control of the suction attachment 6001 and the finger switch of the surgical instrument 6003. Whereas releasable securing of the suction attachment 6001 with the surgical instrument 6003 as shown in FIGS. 6A-6B may be suitable for right handed operation, alternative arrangement may be employed for left handed operation. FIGS. 6D-6E show such alternative arrangement for releasable securing of the suction attachment 6001 with the surgical instrument 6003, which may be suitable for left handed operation.

Figure 7:
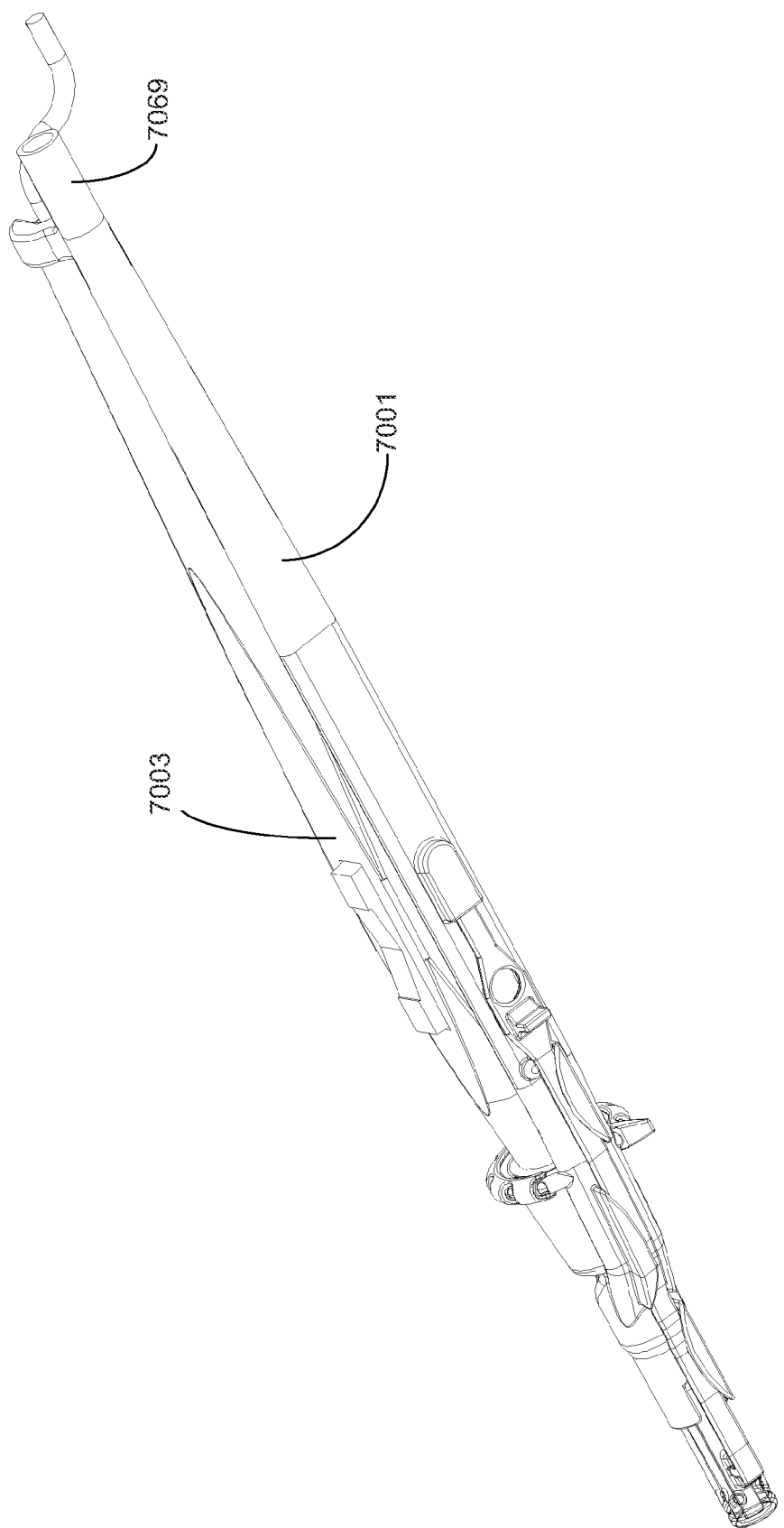
FIG. 7 shows an alternative embodiment of the suction attachment.

FIG. 7 shows an alternative embodiment of the suction attachment 7001 for the surgical instrument 7003. There has been previous discussion herein of the isolation member disposed within the attachment housing for substantially separating transport of liquid and smoke, so that the liquid may be output at the liquid output port while the smoke may be output at a smoke output port. However, in the alternative embodiment shown in FIG. 7, a single output port 7069 may be provided, instead of two ports as discussed previously herein. In the alternative embodiment shown in FIG. 7 the isolation member may be omitted.

Figure 8:
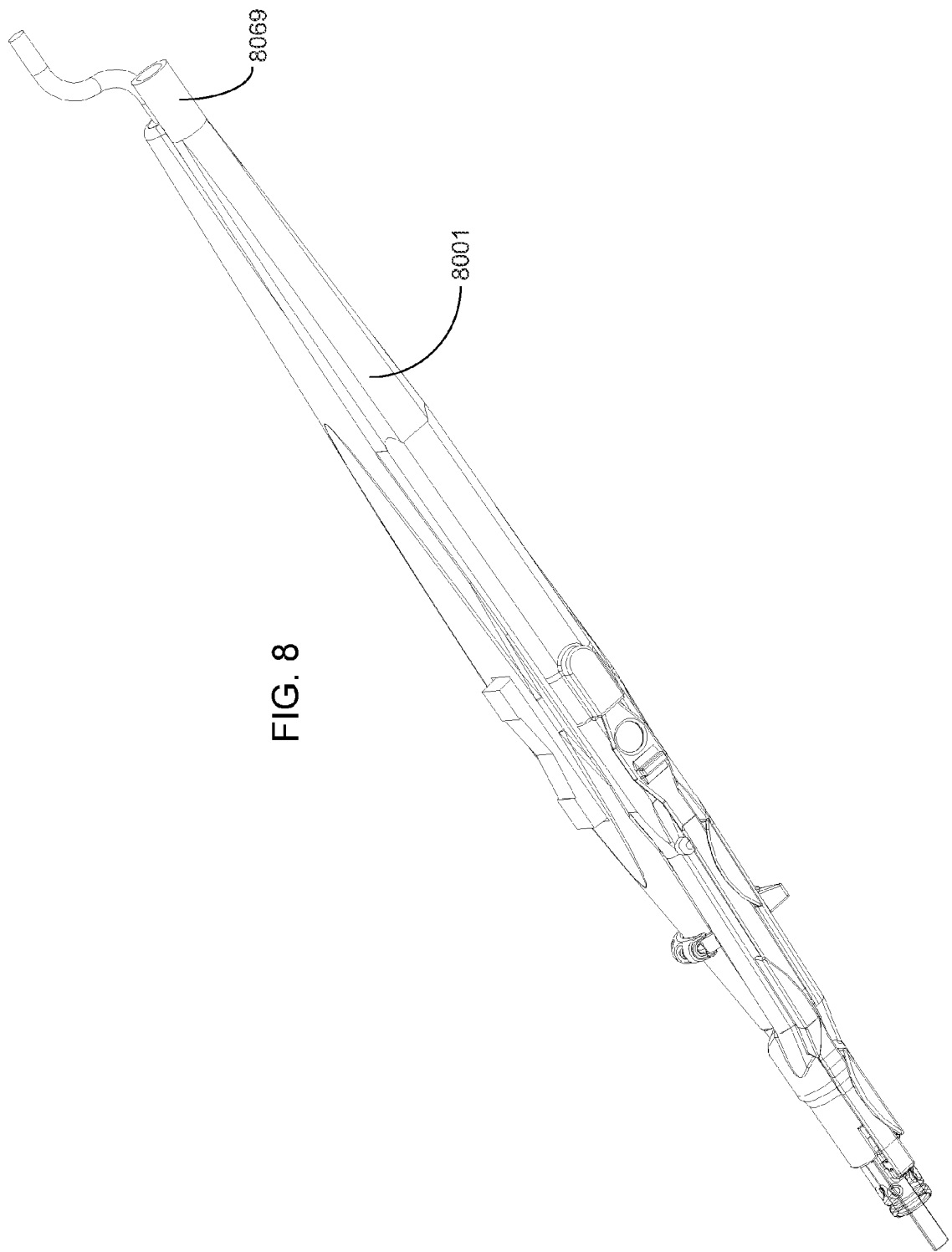
FIG. 8 shows another alternative embodiment, wherein suction capability is made integral with the surgical instrument.

FIG. 8 shows another alternative embodiment, wherein suction capability is made integral with the surgical instrument 8001. In the alternative embodiment shown in FIG. 8, a single output port 8069 may be provided, instead of two ports as discussed previously herein. Further, in the alternative embodiment shown in FIG. 8, features of the attachment housing discussed previously herein need not be separate from the surgical instrument housing, and may be made integral with the surgical instrument. In the alternative embodiment shown in FIG. 8 the engagement members discussed previously herein may be omitted.

Figure 9:
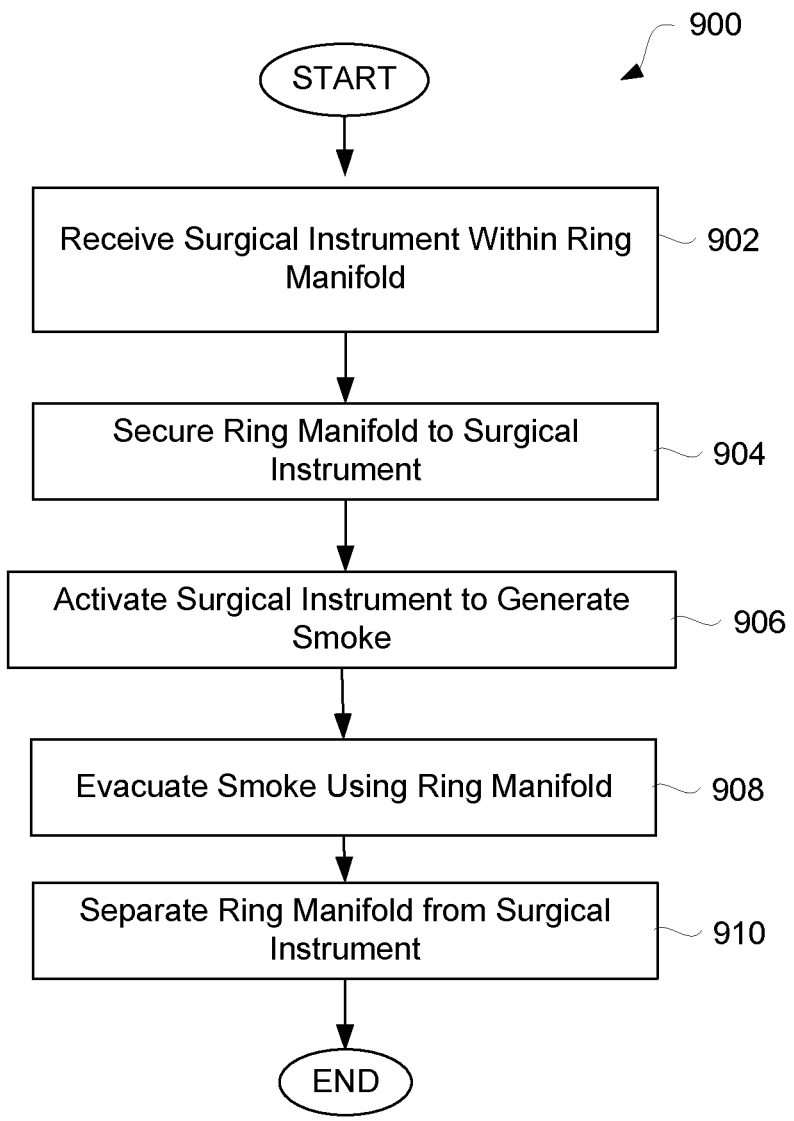
FIG. 9 is a flow diagram of a process for using a surgical instrument that may generate smoke.

FIG. 9 is a flow diagram of a process 900 for using a surgical instrument that may generate smoke. Such process 900 may begin with receiving 902 the surgical instrument within an inner perimeter of a ring manifold, wherein the ring manifold has a plurality of suction intake ports disposed about an outer perimeter of the ring manifold. The process 900 may continue with releasably securing 904 the ring manifold to the surgical instrument. The process 900 may continue with activating 906 the surgical instrument so as to generate smoke. The process 900 may continue with evacuating 908 the smoke using the suction intake ports of the ring manifold. The process 900 may continue with separating 910 the ring manifold from the electrosurgical pencil. The ring manifold may be disposable and separating 910 may further comprise disposing of the ring manifold. Once the ring manifold has been separated from the surgical instrument, the process 900 may end.

Figure 10:
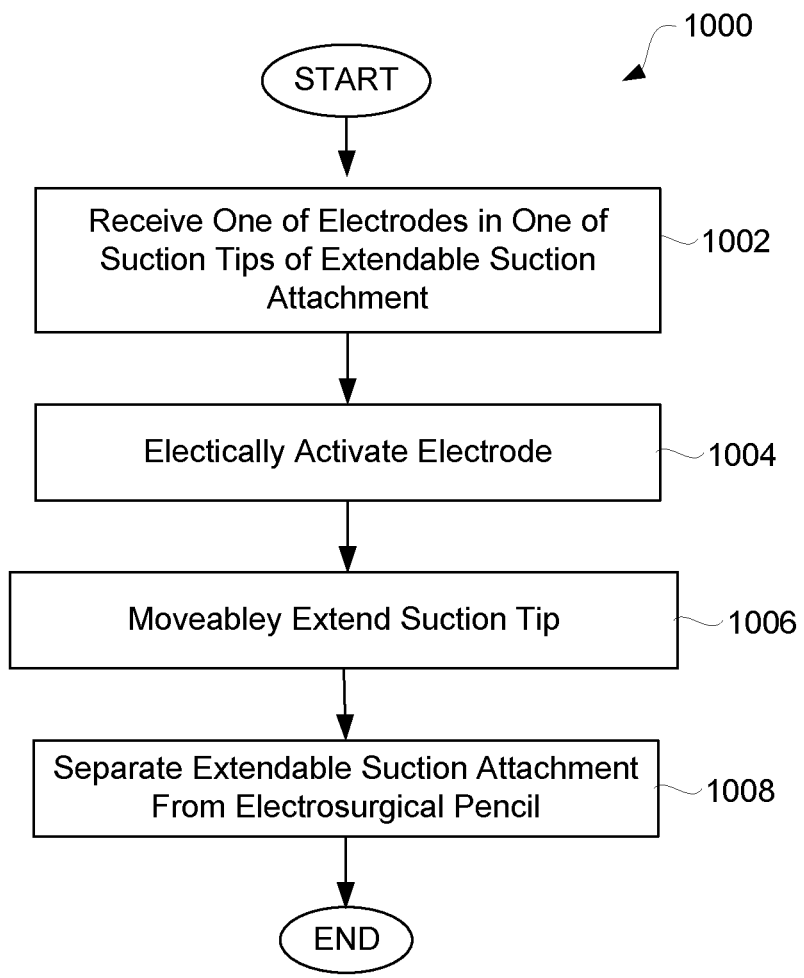
FIG. 10 is a flow diagram of a process for using an electrosurgical pencil that alternatively employs one of a plurality of differently shaped electrocautery electrodes.

FIG. 10 is a flow diagram of a process 1000 for using an electrosurgical pencil that alternatively employs one of a plurality of differently shaped electrocautery electrodes. The process 1000 may begin with receiving 1002 one of the differently shaped electrocautery electrodes in a corresponding respective one of a plurality of differently shaped suction tip extension members of an extendable suction attachment. The process 1000 may continue with electrically activating 1004 the electrocautery electrode. The process 1000 may continue with moveably extending 1006 one of the plurality of differently shaped suction tip extension members. The process 1000 may continue with separating 1008 the extendable suction attachment from the electrosurgical pencil. The extendable suction attachment may be disposable and such separating 1008 may further comprising disposing of the extendable suction attachment. Once the extendable suction attachment has been separated from the electrosurgical pencil, the process 1000 may end.

Figure 11:
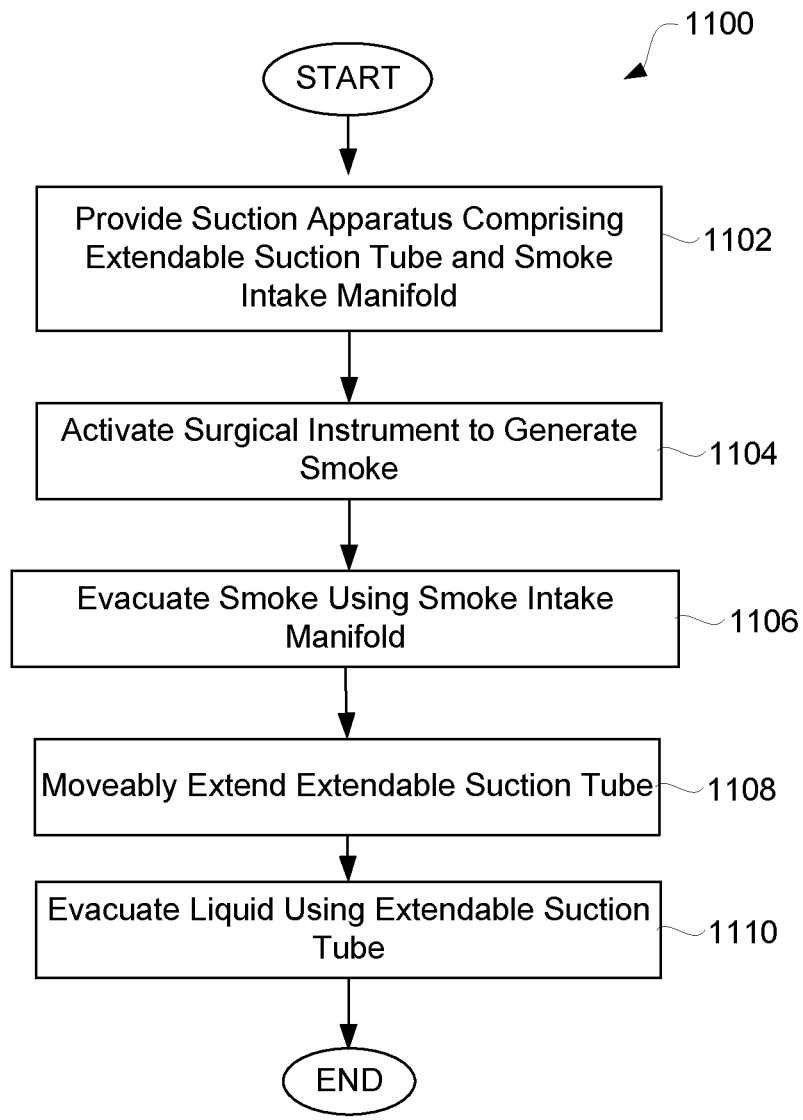
FIG. 11 is a flow diagram of another process for using a surgical instrument that may generate smoke.

FIG. 11 is a flow diagram of another process 1100 for using a surgical instrument that may generate smoke. The process 1100 may begin with providing 1102 a suction apparatus comprising an extendable suction tube and a smoke intake manifold having a plurality of suction ports. The process 1100 may continue with activating 1104 the surgical instrument so as to generate smoke. The process 1100 may continue with evacuating the smoke 1106 using suction intake ports of the smoke intake manifold. The process may continue with moveably extending 1108 the extendable suction tube. The process 1100 may continue with evacuating liquid 1110 using the extendable suction tube during surgical operations with the surgical instrument.

Figure 12:
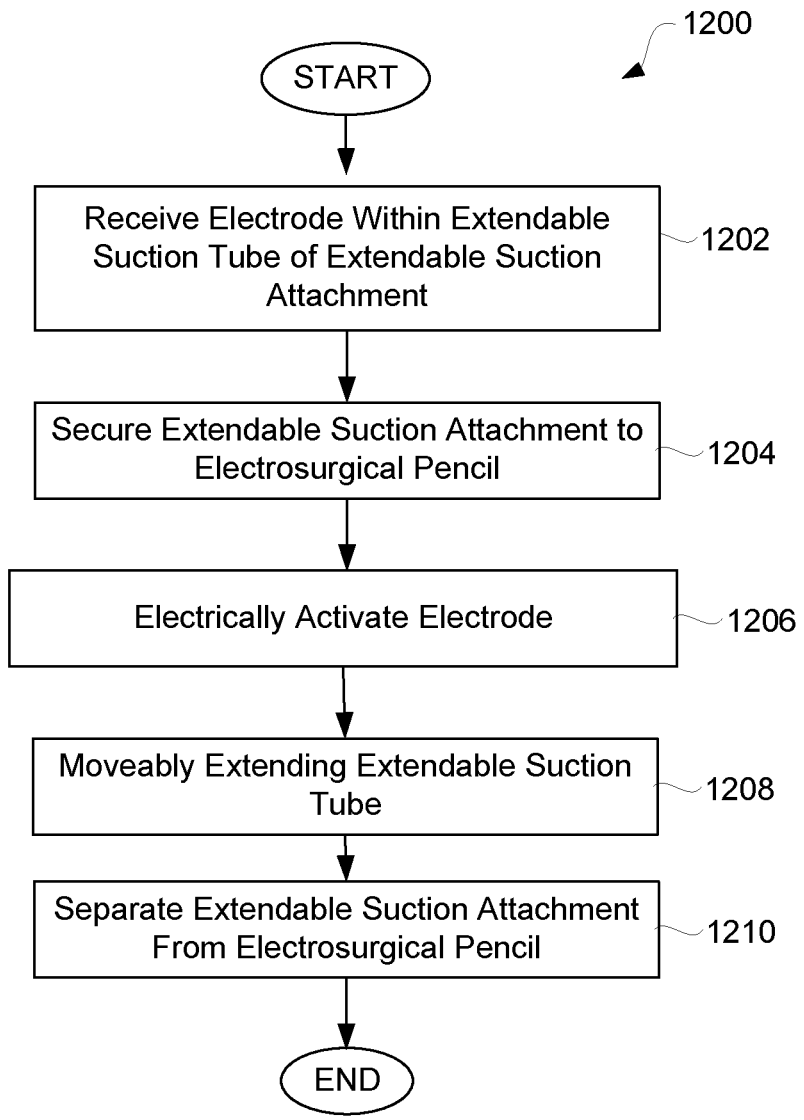
FIG. 12 is a flow diagram of another process for using an electrosurgical pencil.

FIG. 12 is a flow diagram of another process 1200 for using an electrosurgical pencil. The process 1200 may begin with receiving 1202 the electrocautery electrode within a lumen of an extendable suction tube of an extendable suction attachment. The process 1200 may continue with releasably securing 1204 the extendable suction attachment to the electrosurgical pencil. The process 1200 may continue with electrically activating 1206 the electrocautery electrode. The process 1200 may continue with moveably extending 1208 the extendable suction tube of the extendable suction attachment. The foregoing may comprise one handed operation of the extendable suction attachment with the electrosurgical pencil. The process 1200 may continue with separating 1210 the extendable suction attachment from the electrosurgical pencil. The extendable suction attachment may be disposable and the separating 1210 may further comprise disposing of the extendable suction attachment.

The various aspects, features, embodiments or implementations of the invention described above can be used alone or in various combinations.

Different aspects, embodiments or implementations may, but need not, yield one or more of the following advantages. One advantage of the invention may be convenience or efficiency in evacuation of smoke and/or liquid. In turn, health of doctors and other health workers may be promoted by avoiding contact with smoke, once it is evacuated. Another advantage may be flexibility in using various differently shaped electrocautery electrodes. Another advantage may be the foregoing convenience or efficiency of evacuation when using the various differently shaped electrocautery electrodes. Another advantage may be inhibiting spread of infection by separating and disposing of disposable suction attachments.

The many features and advantages of the present invention are apparent from the written description. Further, since numerous modifications and changes will readily occur to those skilled in the art, the invention should not be limited to the exact construction and operation as illustrated and described. Hence, all suitable modifications and equivalents may be resorted to as falling within the scope of the invention.

What is claimed is:

1. A suction apparatus for an electrosurgical pencil that alternatively employs one of a plurality of differently shaped electrocautery electrodes comprising:
   a plurality of differently shaped electrocautery electrodes;
   a plurality of differently shaped suction tip extension members;
   an extendable suction tube comprising a main suction tube alternatively coupled with at least one of a plurality of differently shaped suction tip extension members, wherein each of the differently shaped suction tip extension members is shaped for receiving a corresponding respective one of the differently shaped electrocautery electrodes;
   a housing supportively coupled with the extendable suction tube; and
   an extension control slideably coupled with the housing and coupled with the extendable suction tube for controlling extendable movement of at least one of the differently shaped suction tip extension members over the corresponding respective one of the differently shaped electrocautery electrodes.

2. A suction apparatus as recited in claim 1 wherein each of the suction tip extension members has a respective one of a plurality of differently shaped lumens, so that each of the lumens is shaped for receiving the corresponding respective one of the differently shaped electrocautery electrodes.

3. A suction apparatus as recited in claim 1 wherein each of the suction tip extension members has a respective one of a plurality of different longitudinal dimensions, so that each of the longitudinal dimensions of the suction tip extension members is selected for receiving the corresponding respective one of the differently shaped electrocautery electrodes.

4. A suction apparatus as recited in claim 1 wherein each of the suction tip extension members has a respective one of a plurality of different radial dimensions, so that each of the radial dimensions of the suction tip extension members is selected for receiving the corresponding respective one of the differently shaped electrocautery electrodes.

5. A suction apparatus as recited in claim 1 wherein the suction apparatus is adapted for receiving at least one electrode extender for alternatively coupling with one of the plurality of differently shaped electrocautery electrodes.

6. A suction apparatus as recited in claim 1 wherein at least one of the suction tip extension members is adapted for receiving at least one electrode extender for alternatively coupling with one of the plurality of differently shaped electrocautery electrodes.

7. A suction apparatus as recited in claim 1 further comprising an engagement member for releasably securing the suction apparatus to the electrosurgical pencil.

8. A suction apparatus as recited in claim 1 wherein the suction apparatus is separable from the electrosurgical pencil.

9. A suction apparatus as recited in claim 1 wherein the suction apparatus is disposable.

10. A suction apparatus as recited in claim 1 further comprising at least one movement limiting slot coupled with the housing for limiting movement of at least one of the differently shaped suction tip extension members to a preselected full extent over the corresponding respective one of the differently shaped electrocautery electrodes.

11. A suction apparatus as recited in claim 1 further comprising at least one movement limiting slot coupled with the housing for limiting at least one of:
   movement of at least one of the differently shaped suction tip extension members to a preselected full extent over the corresponding respective one of the differently shaped electrocautery electrodes; and
   movement of at least one of the differently shaped suction tip extension members to a preselected retraction extent over the corresponding respective one of the differently shaped electrocautery electrodes, so as to expose the corresponding respective one of the differently shaped electrocautery electrodes outside of at least one of the differently shaped suction tip extension members.

12. A suction apparatus for an electrosurgical pencil as recited in claim 1 further comprising:
   a first movement limiting slot coupled with the housing for limiting movement of at least one of the differently shaped suction tip extension members to a preselected full extent over the corresponding respective one of the differently shaped electrocautery electrodes; and
   an opposing movement limiting slot coupled with the housing for limiting movement of at least one of the differently shaped suction tip extension members to a preselected retraction extent over the corresponding respective one of the differently shaped electrocautery electrodes, so as to expose the corresponding respective one of the differently shaped electrocautery electrodes outside of at least one of the differently shaped suction tip extension members.

13. A suction attachment for an electrosurgical pencil that alternatively employs one of a plurality of differently shaped electrocautery electrodes comprising:
   a plurality of differently shaped electrocautery electrodes;
   a plurality of differently shaped suction tip extension members, wherein each of the differently shaped suction tip extension members is shaped for receiving a corresponding respective one of the differently shaped electrocautery electrodes;
   an attachment housing for fluid coupling with one of the plurality of differently shaped suction tip extension members; and
   an engagement member for releasably securing the suction attachment to the electrosurgical pencil.

14. A suction attachment as recited in claim 13 wherein the suction attachment is separable from the electrosurgical pencil.

15. A suction attachment as recited in claim 13 wherein the suction attachment is disposable.

16. A suction attachment as recited in claim 13 wherein the suction attachment is adapted for receiving at least one electrode extender for alternatively coupling with one of the plurality of differently shaped electrocautery electrodes.

17. A suction attachment as recited in claim 13 wherein at least one of the suction tip extension members is adapted for receiving at least one electrode extender for alternatively coupling with one of the plurality of differently shaped electrocautery electrodes.

18. A method for using an electrosurgical pencil that alternatively employs one of a plurality of differently shaped electrocautery electrodes comprising:
   receiving one of the differently shaped electrocautery electrodes in a corresponding respective one of a plurality of differently shaped suction tip extension members of an extendable suction attachment;
   electrically activating the electrocautery electrode; and
   moveably extending one of the plurality of differently shaped suction tip extension members.

19. A method as recited in claim 18 further comprising separating the extendable suction attachment from the electrosurgical pencil.

20. A method as recited in claim 19 wherein the extendable suction attachment is disposable and further comprising disposing of the extendable suction attachment.

* * * * *